United States Patent
O'Brien et al.

(10) Patent No.: US 11,890,080 B2
(45) Date of Patent: Feb. 6, 2024

(54) SELF-CALIBRATING GLUCOSE MONITOR

(71) Applicant: Medtronic, Inc., Minneapolis, MN (US)

(72) Inventors: Richard J. O'Brien, Hugo, MN (US); Lilian Kornet, Eijsden (NL); Richard N. Cornelussen, Maastricht (NL); Alfonso Aranda Hernandez, Shoreview, MN (US); Raphael Schneider, Maastricht (NL)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 18/173,570

(22) Filed: Feb. 23, 2023

(65) Prior Publication Data

US 2023/0190116 A1   Jun. 22, 2023

Related U.S. Application Data

(63) Continuation of application No. 17/168,761, filed on Feb. 5, 2021, now Pat. No. 11,607,140.

(51) Int. Cl.
*A61B 5/02* (2006.01)
*A61B 5/0205* (2006.01)
(Continued)

(52) U.S. Cl.
CPC .......... *A61B 5/0205* (2013.01); *A61B 5/1455* (2013.01); *A61B 5/1495* (2013.01);
(Continued)

(58) Field of Classification Search
None
See application file for complete search history.

(56) References Cited

U.S. PATENT DOCUMENTS 9,282,895 B2    3/2016   Wenzel et al.
2010/0298673 A1  11/2010  Herrmann
(Continued)

FOREIGN PATENT DOCUMENTS

WO   2009070675 A2   6/2009
WO   2009142853 A1   11/2009

OTHER PUBLICATIONS

Gao et al., "Diabetes Mellitus, Fasting Blood Glucose Concentration, and Risk of Vascular Disease: a Collaborative Meta-Analysis of 102 Prospective Studies," The Lancet, vol. 375,0 Jun. 26, 2010, pp. 2215-2222.
Hasslacher et al., "Diabetes Prevalence in Patients with Bradycardiac Arrhythmias," Acta Diabetologica Latina, vol. 14, No. 5-6, Sep.-Dec. 1977, pp. 229-234.

*Primary Examiner* — Ankit D Tejani
(74) *Attorney, Agent, or Firm* — Shumaker & Sieffert, P.A.

(57) ABSTRACT

A medical system including processing circuitry configured to receive a cardiac signal indicative of a cardiac characteristic of a patient from sensing circuitry and configured to receive a glucose signal indicative of a glucose level of the patient. The processing circuitry is configured to formulate a training data set including one or more training input vectors using the cardiac signal and one or more training output vectors using the glucose signal. The processing circuitry is configured to train a machine learning algorithm using the formulated training data set. The processing circuitry is configured to receive a current cardiac signal from the patient and determine a representative glucose level using the current cardiac signal and the trained machine learning algorithm.

20 Claims, 7 Drawing Sheets

(51) Int. Cl.
  *A61B 5/1495*   (2006.01)
  *A61B 5/318*    (2021.01)
  *A61B 5/36*     (2021.01)
  *A61B 5/358*    (2021.01)
  *A61B 5/355*    (2021.01)
  *A61B 5/1455*   (2006.01)
  *A61B 5/00*     (2006.01)
  *A61B 5/145*    (2006.01)
  *G16H 50/20*    (2018.01)
  *A61B 5/352*    (2021.01)
  *A61B 5/024*    (2006.01)

(52) U.S. Cl.
  CPC .......... *A61B 5/14532* (2013.01); *A61B 5/318* (2021.01); *A61B 5/352* (2021.01); *A61B 5/355* (2021.01); *A61B 5/358* (2021.01); *A61B 5/36* (2021.01); *A61B 5/6802* (2013.01); *G16H 50/20* (2018.01); *A61B 5/02405* (2013.01); *A61B 2560/0223* (2013.01)

(56) References Cited

U.S. PATENT DOCUMENTS

| | | |
|---|---|---|
| 2021/0228090 A1 | 7/2021 | Martin et al. |
| 2021/0375448 A1 | 12/2021 | Derdzinski et al. |
| 2021/0401330 A1 | 12/2021 | Frank et al. |
| 2022/0248965 A1 | 8/2022 | O'brien et al. |
| 2022/0346676 A1 | 11/2022 | Pecchia et al. |

OTHER PUBLICATIONS

International Search Report and Written Opinion of International Application No. PCT/US2022/014646, dated May 12, 2022, 6 pp.
Kristensen et al., "Prevalence of Prediabetes and Undiagnosed Diabetes in Patients with HFpEF and HFrEF and Associated Clinical Outcomes," Cardiovascular Drugs and Therapy, vol. 31, No. 5, Sep. 25, 2017, pp. 545-549.
Notice of Allowance from U.S. Appl. No. 17/168,761 dated Nov. 23, 2022, 11 pp.
Porumb et al., "Precision Medicine and Artificial Intelligence: A Pilot Study on Deep Learning for Hypoglycemic Events Detection based on ECG," Scientiifc Reports, vol. 10, No. 170, Jan. 13, 2020, 16 pp.

SELF-CALIBRATING GLUCOSE MONITOR

CROSS-REFERENCE TO RELATED APPLICATIONS

This application is a continuation of U.S. application Ser. No. 17/168,761, filed Feb. 5, 2021, the entire contents of which are incorporated by reference herein.

TECHNICAL FIELD

This disclosure is related to a medical system for evaluating a glucose level of a patient.

BACKGROUND

Physiological characteristic sensors may be use in a variety of specialized applications. For example, implantable sensors may be used in glucose monitoring systems to facilitate treatment of diabetes, such as monitoring glucose levels over time for adjusting a treatment regimen that includes regular administration of insulin to a patient. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin based on a monitored glucose level.

SUMMARY

Examples of a medical system disclosed here include processing circuitry configured to receive a cardiac signal from sensing circuitry and a glucose signal from a glucose sensor. The cardiac signal is indicative of a cardiac characteristic of a patient. The glucose signal is indicative of a glucose level of the patient. The processing circuitry is configured to formulate a training data set including one or more training input vectors using the cardiac signal and one or more training output vectors using the glucose signal. The processing circuitry is configured to train a machine learning algorithm using the formulated training data set. Using the trained machine learning algorithm, the processing circuitry is configured to determine a representative glucose level using a current cardiac signal from the patient. The processing circuitry may be configured to deactivate the glucose sensor once the machine learning algorithm is sufficiently trained to provide the representative glucose level, potentially extending a life of the glucose sensor.

In an example, medical system comprises: a glucose sensor configured to determine a glucose level in a patient; and processing circuitry operably coupled to the glucose sensor, the processing circuitry configured to: receive a glucose signal indicative of the glucose level from the glucose sensor, receive a cardiac signal indicative of a cardiac characteristic of the patient, associate the glucose signal with the cardiac signal, formulate one or more training data sets including a training input vector and a training output vector, wherein the training input vector is representative of the cardiac signal and the training output vector is representative of the glucose signal associated with the cardiac signal, train a machine learning algorithm using the one or more training data sets, and determine a representative glucose level using the trained machine learning algorithm and a current cardiac signal, wherein the current cardiac signal is indicative of a current cardiac characteristic of the heart of the patient.

In an example, a medical system comprises: a glucose sensor configured to determine a glucose level in a patient; sensing circuitry configured to sense a cardiac characteristic of a heart of the patient; processing circuitry operably coupled to the glucose sensor and the sensing circuitry, the processing circuitry configured to: receive an cardiac signal indicative of the cardiac characteristic from the sensing circuitry, identify a cardiac marker using the cardiac signal, receive a glucose signal indicative of the glucose level from the glucose sensor, associate the cardiac marker with the glucose signal, formulate one or more training data sets including a training input vector and a training output vector, wherein the training input vector is representative of the cardiac signal and the training output vector is representative of the glucose signal associated with the glucose signal, train a machine learning algorithm using the one or more training data sets, and determine a representative glucose level using the trained machine learning algorithm and a current cardiac signal received from the sensing circuitry, wherein the current cardiac signal is indicative of a current cardiac characteristic of the heart of the patient; and a housing mechanically supporting the glucose sensor and the processing circuitry, In an example, a method comprises: receiving, using processing circuitry, an ECG signal indicative of an electrocardiogram of a heart of a patient from sensing circuitry configured to sense the electrocardiogram, receiving, using the processing circuitry, a glucose signal indicative of a glucose level of the patient from a glucose sensor configured to determine the glucose level in the patient, associating, using the processing circuitry, the ECG signal with the glucose level, formulating, using the processing circuitry, one or more training data sets including a training input vector and a training output vector, wherein the training input vector is representative of the ECG signal and the training output vector is representative of the glucose signal associated with the ECG signal, training, using the processing circuitry, a machine learning algorithm using the one or more training data sets, and determining, using the processing circuitry, a representative glucose level using the trained machine learning algorithm and a current cardiac signal, wherein the current cardiac signal is indicative of a current cardiac characteristic of the heart of the patient.

The details of one or more examples are set forth in the accompanying drawings and the description below. Other features, objects, and advantages will be apparent from the description and drawings, and from the claims.

DETAILED DESCRIPTION

Figure 1:
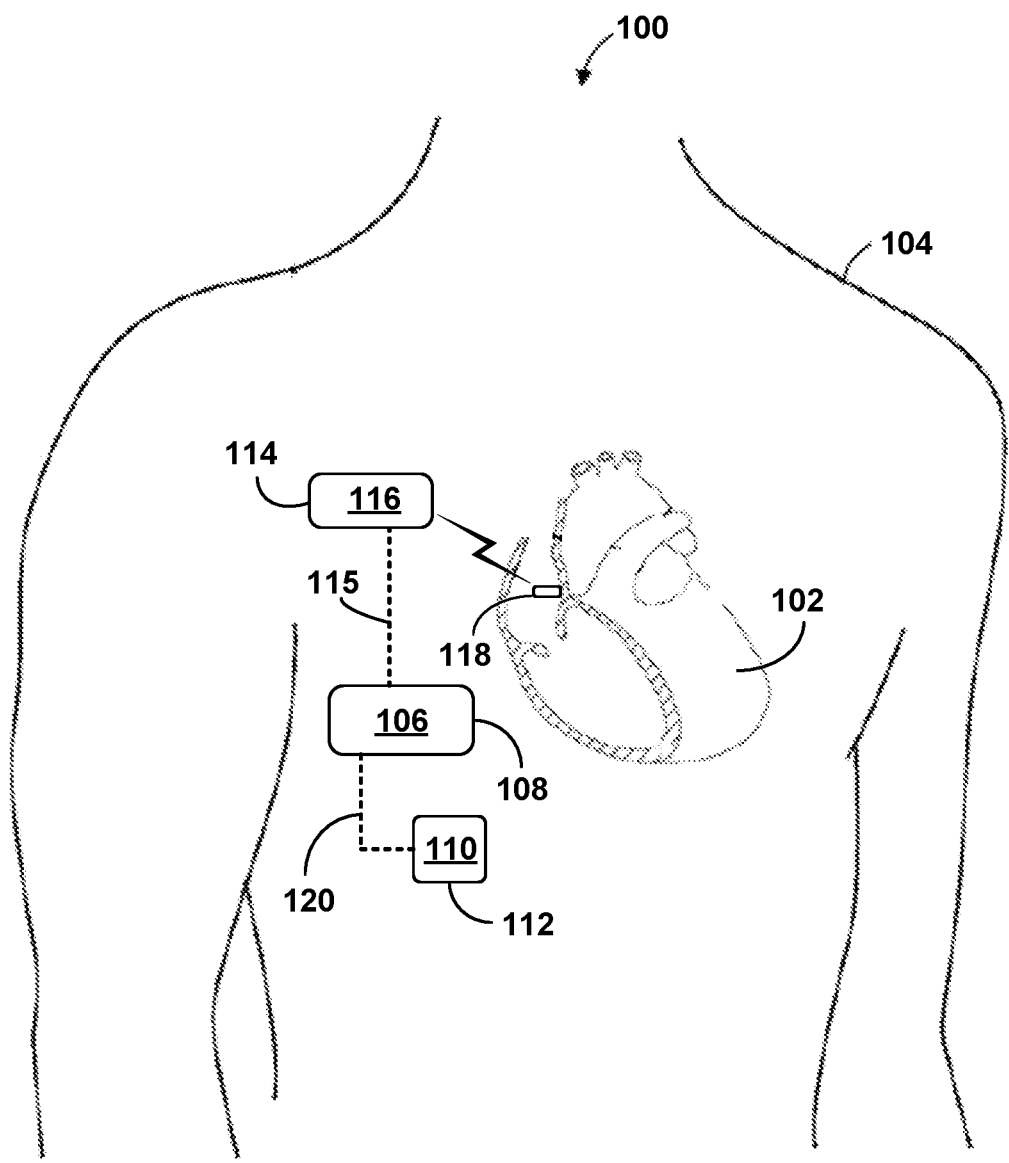
FIG. 1 is a conceptual diagram illustrating an example medical system including a glucose sensor.

This disclosure describes a medical system including processing circuitry configured to train a machine learning algorithm using a cardiac characteristic of a heart and a glucose level of a patient. The cardiac characteristic may be representative of the cardiac electrical activity of the heart of the patient, such as an electrocardiogram (ECG), an electrogram (EGM), or another measure. The medical system may include sensing circuitry to provide the cardiac characteristic of the patient and a glucose sensor to provide the glucose level of the patient. The processing circuitry is configured to associate some portion of the cardiac characteristic with a glucose level received and formulate a training data set to train the machine learning algorithm. Subsequent to training, the medical system is configured to determine a representative glucose level of the patient based on a current cardiac characteristic reflecting current cardiac activity of the patient. The medical system may thus substantially personalize the machine learning algorithm to the cardiac characteristics of a patient by formulating the training set and training the machine learning algorithm using physiological indications individual to the patient. In examples, the processing circuitry is configured to perform a calibration check of the trained machine learning algorithm by comparing the representative glucose level indicated to a current glucose level of the patient, and further training or re-training the machine learning algorithm based on the comparison.

The medical system may include a wearable, implantable, and/or portable device including a housing configured to contact a body (e.g., a torso) of the patient. The housing may mechanically support one or processors configured to receive a cardiac signal indicative of the cardiac characteristic of the patient and a glucose signal indicative of the glucose level of the patient. The processing circuitry is configured to formulate one or more training data sets using the cardiac signal and the glucose signal. In examples, the one or more training data sets include a plurality of training input vectors representative of the cardiac signal and a plurality of training output vectors representative of the glucose signal, with each training input vector associated with a corresponding training output vector. The one or more processors are configured to train the machine learning algorithm with the training data set such that the processing circuitry may subsequently receive a current cardiac signal indicative of cardiac activity of the patient and determine a representative glucose level using the current cardiac signal. In examples, the one or more processors comprise a memory and one or more processing circuits configured to enact the machine learning algorithm.

In examples, the housing includes a glucose sensor configured to provide the glucose signal indicative of the glucose level to the one or more processors. The processing circuitry may be configured to cause the glucose sensor to activate to provide the glucose signals (e.g., while formulating the training data set), and may be configured to cause the glucose sensor to deactivate when the glucose signals are no longer actively required (e.g., once the training data set is formulated and/or once the machine learning algorithm is trained). Thus, the medical system may be configured to substantially reduce and/or minimize the activated time of an on-board glucose sensor, potentially extending the life of the glucose sensor and decreasing the need for periodic replacement.

In some examples, the housing of the wearable, implantable, and/or portable device mechanically supports a plurality of individual glucose sensors. The processing circuitry may be configured to selectively expose a first individual glucose sensor in the plurality to, for example, the interstitial fluid or blood of a patient to generate the glucose signal when required (e.g., while formulating training data and/or conducting a calibration check). The processing circuitry may be configured to deactivate the first individual glucose sensor and activate a second individual glucose sensor in the plurality when a replacement criteria for the first individual glucose sensor is met (e.g., when the processing circuitry detects a degraded signal, following the elapse of a chronological period of use, and/or for another reason).

The processing circuitry may be configured to periodically perform a calibration check of the trained machine learning algorithm by determining a current glucose level of the patient using the glucose sensor and comparing the current glucose level to a representative glucose level determined for the patient by the trained machine learning algorithm. Based on the comparison, the processing circuitry may be configured to formulate additional training data and further train or re-train the machine learning algorithm using the additional training data. The processing circuitry may thus be configured to substantially adjust the response of the machine learning algorithm based on individual changes of the physiological parameters of the patient.

In examples, the processing circuitry is configured to identify a cardiac marker using the cardiac signal and associate the cardiac marker with a glucose signal provided by the glucose sensor. The cardiac marker may be is at least one of, for example, a heart rate variability (HRV), a QT internal variability (QTV), a corrected QT interval (QTc), an ST interval, an ST elevation, a T wave amplitude, a T-peak to T-end interval, a T slope, a T-wave area, a T-wave asymmetry, an R-wave amplitude, a T-wave amplitude, and/or another identifiable characteristic of the cardiac signal of the patient. The processing circuitry may be configured to identify a value of the cardiac marker within an segment of the cardiac signal received over a time interval (e.g., an ECG segment and/or an EGM segment), and may be configured to associate a glucose signal received from the glucose sensor with a value of the cardiac marker. The processing circuitry may formulate a training input vector representative of the value of the cardiac marker and a corresponding training output vector representative of the received glucose signal. In examples, the processing circuitry identifies a value of the cardiac marker and an associated glucose signal for a plurality of segments of the cardiac signal, and formulates a training input vector and corresponding training output vector for each segment.

The medical system may include sensing circuitry configured to sense the cardiac characteristic of the patient and generate the cardiac signal and/or cardiac marker. The sensing circuitry may be configured to communicate the cardiac signal and/or cardiac marker to the processing circuitry. For example, the medical system may be at least partially incorporated into a medical device including a housing which mechanically supports the processing circuitry and the sensing circuitry. In some examples, the medical device includes one or more electrodes configured to contact the patient and sense the cardiac characteristic of the heart. The housing of the medical device may mechanically support the electrodes. In other examples, the processing circuitry may be configured to receive the cardiac signal and/or cardiac marker from another system or device configured to detect and communicate the cardiac signal and/or cardiac marker. For example, the processing circuitry may be configured to receive the cardiac signal and/or cardiac marker from an implantable and/or wearable cardiography system configured to sense a cardiac signal and/or cardiac marker of the patient and communicate the cardiac signal and/or cardiac marker to the processing circuitry.

In some examples, the medical system includes an infusion device configured to provide a therapeutic fluid (e.g., insulin) to the patient. For example, the medical system may include a fluid delivery cannula configured to deliver a fluid (e.g., insulin) to the patient. The medical system may include a fluid pump (e.g., an insulin pump) configured for fluid communication with the fluid delivery cannula. The fluid pump may be configured to deliver the fluid to the fluid delivery cannula from a fluid reservoir of the medical system. The fluid reservoir may be, for example, a volume defined by a detachable fluid cartridge configured to mechanically engage a housing of the medical system and to establish a fluidic connection with the fluid pump. In examples, the processing circuitry is configured to control an operation of the fluid pump. For example, the processing circuitry may be configured to cause the fluid pump to commence, continue, and/or cease causing transportation of fluid from the fluid reservoir through the fluid delivery cannula based on the representative glucose level determined by the trained machine learning algorithm. In some examples, when the medical system is at least partially incorporated into a medical device including a housing, the housing may mechanically support the fluid delivery cannula, the fluid pump, the fluid reservoir, and/or other components of an infusion device.

The medical system may include a user interface for presenting information to and receiving input from the patient. For example, the user interface may be configured to generate a visual display viewable by the patient and providing information such as a representative glucose level determined at a discrete chronological time or over a time interval, a graph of representative glucose levels, a period of use since the most recent training and/or calibration check, a status of an individual glucose sensor, an accuracy or alert based on a calibration check, and/or other information arising through operation of the medical system. The user interface may be configured to cause the processing circuitry to perform certain functions based on an input from the patient. For example, user interface may cause the processing circuitry to formulate a training data set, train the machine learning algorithm, perform a calibration check of the trained machine learning algorithm, cause a glucose sensor to generate a current glucose signal, and/or other functions.

In examples, the medical system may be implemented using one or more computer programs implemented on programmable computers, such as computers that include, for example, processing capabilities, data storage (e.g., volatile or nonvolatile memory and/or storage elements), input devices, and output devices. Program code and/or logic described herein may be applied to input data to perform the functionality described herein and generate desired output information. The programs may be stored on any suitable device, e.g., a storage media, readable by a general or special purpose program running on a computer system (e.g., including processing apparatus) and configuring the computer system to perform functions described herein. Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g., a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a conceptual diagram of an example medical system 100 configured to determine a representative glucose level based on a cardiac signal indicative of the cardiac activity of a heart 102 of a patient 104. Medical system 100 includes processing circuitry 106 mechanically supported within a housing 108 and a glucose sensor 110 supported within a sensor housing 112. In examples, housing 108 mechanically supports both processing circuitry 106 and glucose sensor 110.

Processing circuitry 106 is configured to receive a cardiac signal (e.g., an ECG or EGM signal) indicative of a cardiac characteristic of heart 102 of patient 104. In examples, processing circuitry 106 is configured to receive the cardiac signal from sensing circuitry 116 of cardiography system 114 via a communication link 115. Cardiography system 114 may be configured to sense and communicate the cardiac signal from a position outside of heart 102 and/or using additional devices located in closer proximity to heart 102, such as sensor 118. Sensing circuitry 116 may be configured to sense the cardiac characteristic of heart 102 and communicate the cardiac signal to processing circuitry 106 (e.g., via communication link 115). Processing circuitry 106 is further configured to receive a glucose signal indicative of a glucose level of patient 104 from glucose sensor 110. For example, processing circuitry 106 may be configured to receive the glucose signal via a communication link 120.

Processing circuitry 106 is configured to use a machine learning algorithm to indicate a representative glucose level indicative of a glucose level of patient 104 using a current cardiac signal. Processing circuitry 106 configured to train the machine learning algorithm to indicate the representative glucose level using the current cardiac signal. Processing circuitry 106 is configured to formulate one or more training data sets using the cardiac signal and glucose signal generated from the physiological characteristics of patient 104, then train the machine learning algorithm using the training data set. The trained machine learning algorithm is thus trained using training data personalized to patient 104, rather than training data aggregated from a plurality of patients. Such personalized training data may improve the accuracy of the representative glucose level obtained when the trained machine learning algorithm receives a current cardiac signal and/or cardiac marker indicative of the cardiac activity of patient 104 and maps the cardiac signal and/or cardiac marker to an output glucose level to obtain the representative glucose level.

Processing circuitry 106 is thereby configured to determine a representative glucose level of patient 104 using a current cardiac signal and/or cardiac marker of patient 104 without the necessity for an attendant current glucose signal from glucose sensor 110. The determination of the representative glucose level of patient 104 without the necessity for the attendant current glucose signal may extend the operational life of glucose sensor 110. In examples, processing circuitry 106 is configured to cause glucose sensor 110 to activate and/or deactivate based on a command signal generated by processing circuitry 106. For example, while formulating the training data set for the machine learning algorithm, processing circuitry might issue a command signal causing glucose sensor 110 to activate (e.g., establish an activated configuration) and commence sensing a glucose level within the blood or interstitial fluid of patient 104. Glucose sensor 110 may be configured to periodically and/or substantially continuously communicate a glucose signal indicative of the glucose level to processing circuitry 106 while activated. Processing circuitry 106 may utilize the glucose signal received from glucose sensor 110 in conjunction with a cardiac signal received from cardiography system 114 (e.g., sensing circuitry 116) to formulate a training data set including a plurality of training input vectors and associated training output vectors. When a sufficient training data set is obtained, processing circuitry 106 may then issue a command causing glucose sensor 110 to deactivate (e.g., establish a deactivated configuration) and substantially cease generating the glucose signal, potentially extending the life of glucose sensor 110. Glucose sensor 110 may be configured to generate the glucose signal indicative of the glucose level in any manner, including sensing of electrochemical potentials, near-infra-red spectroscopy, impedance spectroscopy, Raman spectroscopy, tomography, photoacoustics, and/or other methods. A variety of glucose sensing methods may be employed, such as methods based on monitoring the optical properties of intrinsically fluorescent or labeled enzymes, their co-enzymes and co-substrates, the measurement of the products of enzymatic oxidation of glucose by glucose oxidase, the use of synthetic boronic acids, the use of Concanavalin A, the application of other glucose-binding proteins, and/or other methods.

For example, glucose sensor 110 may include an electrode (e.g., an electrooxidizing anode) configured to cause an oxidation of glucose using a catalyst included in glucose sensor 110, such as a glucose oxidase enzyme. Glucose sensor 110 may include an electrode (e.g., an electrooxidizing anode) configured to receive electrical power from a battery within medical system 100 to cause the oxidation. Processing circuitry 106 may be configured to activate glucose sensor 110 by causing the electrode to receive the electrical power. Processing circuitry 106 may be configured to deactivate glucose sensor 110 to prevent and/or minimize the electrical power received by the electrode. Deactivating glucose sensor 110 to reduce and/or substantially prevent the oxidation of glucose may extend the life of the electrode by reducing degradation of the included catalyst, or other portions of glucose sensor 110. For example, processing circuitry 106 may be configured to activate glucose sensor 110 when one or more glucose signals are required to formulate the training data set and/or perform a calibration check of the trained machine learning algorithm, and may be configured to deactivate glucose sensor 110 when processing circuitry 106 utilizes the trained machine learning algorithm and a current cardiac signal from cardiography system 114 (e.g., sensing circuitry 116) to determine a representative glucose level. Such selective activation and deactivation may extend the useful life of glucose sensor 110.

Processing circuitry 106 is configured to initially train the machine learning algorithm using the cardiac signal (e.g., received from cardiography system 114) and the glucose signal received from glucose sensor 110. To train the machine learning algorithm, processing circuitry 106 may be configured to formulate a training data set using the cardiac signal and the glucose signal indicative of the physiological characteristics of patient 104. In examples, the training data set formulated includes a plurality of training input vectors representative of the cardiac signal sensed for patient 104 and a plurality of training output vectors representative of the glucose signal sensed for patient 104, with each training input vector associated with a corresponding training output vector. The plurality of training input vectors and the plurality of training output vectors are thus personalized to the physiology of patient 104. Processing circuitry 106 is configured to train the machine learning algorithm using the personalized training data set, such that the trained machine learning algorithm is trained to output a representative glucose level for patient 104 when provided with an input vector representative of a current cardiac signal sensed for patient 104 (e.g., sensed by cardiography system 114).

Figure 2:
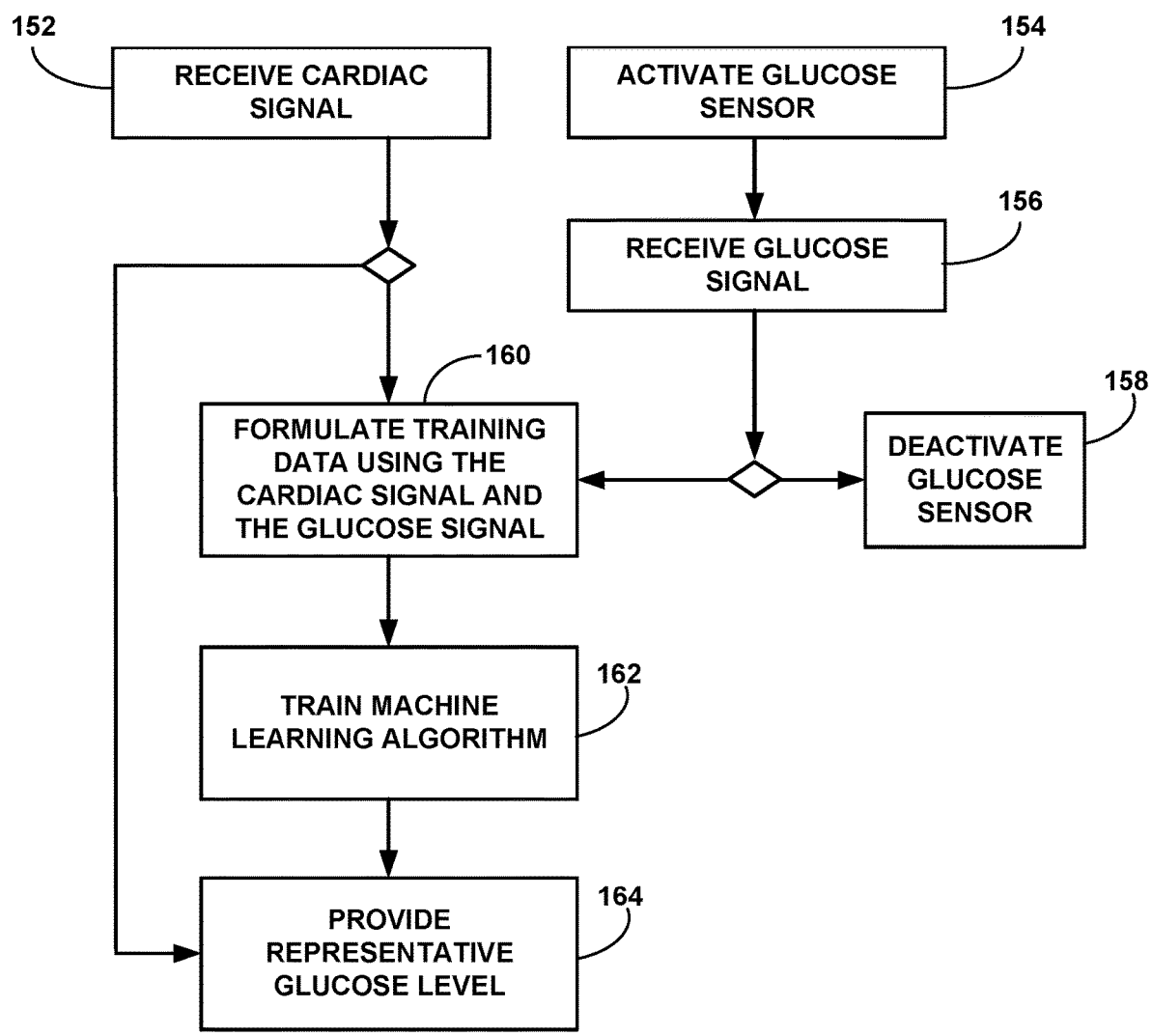
FIG. 2 is a example flow diagram for processing circuitry of a medical system.

FIG. 2 illustrates a flow diagram of an example technique which may be utilized by processing circuitry 106 to determine a representative glucose level of patient 104 based on a cardiac signal indicative of a physiological characteristic of heart 102. Processing circuitry 106 may utilize all or any portion of the technique illustrated by FIG. 2. As illustrated in FIG. 2, processing circuitry 106 receives a cardiac signal indicative of a cardiac characteristic of heart 102 from cardiography system 114 (e.g., sensing circuitry 116) (152). Processing circuitry 106 may activate glucose sensor 110 (154), and receive a glucose signal indicative of a glucose level of patient 104 from glucose sensor 110 (156). Processing circuitry 106 may deactivate glucose sensor 110 (158) once the glucose signals are no longer actively required (e.g., once the training data set is formulated) in order to, for example, extend an operational life of glucose sensor 110 and/or another component of medical system 100.

Processing circuitry 106 utilizes the cardiac signal and the glucose signal received to formulate a training data set (160). In examples, the training data set includes a plurality of training input vectors indicative of the cardiac signal from cardiography system 114 (e.g., sensing circuitry 116), with each training input vector associated with a training output vector indicative of the glucose signal from glucose sensor 110. In examples, processing circuitry 106 is configured to formulate a given training input vector comprising the training data set by receiving a cardiac signal from cardiography system 114 and dividing the cardiac signal into a segment, where the cardiac segment is the cardiac signal received over a time interval. In examples, cardiography system 114 may be configured to divide the cardiac signal into a segment and provide the segment to processing circuitry 106. Processing circuitry 106 may be configured to identify an cardiac marker indicative of and/or derived from the cardiac signal and/or cardiac segment. The cardiac marker may be one or more identifiable physiological characteristics of heart 102 indicated by the cardiac signal of heart 102. Processing circuitry 106 may formulate the given input vector by defining one or more elements of the given input vector, where the one or more elements are indicative of the cardiac signal, the cardiac segment, and/or the cardiac marker identified over the time interval.

Processing circuitry 106 may be configured to formulate a training output vector associated with the given input vector by receiving and/or sampling a glucose signal from glucose sensor 110. Processing circuitry 106 may formulate the associated training output vector by defining one or more elements of the associated training output vector, where the one or more elements are indicative of the received and/or sampled glucose signal. In some examples, processing circuitry 106 is configured to receive and/or sample the glucose signal utilized to formulate the associated output vector substantially within the time interval of the cardiac segment utilized to formulate the given input vector. In some examples, processing circuitry 106 is configured to receive and/or sample the glucose signal utilized to formulate the associated training output vector outside of the time interval of the cardiac segment utilized to formulate the given input vector. For example, processing circuitry 106 may be configured to receive and/or sample the glucose signal utilized to formulate an associated training output vector after the time interval of the cardiac segment utilized to formulate the given input vector has elapsed, in order to account for, for example, a time lag in glucose transport when sensing glucose level in interstitial fluid of patient 104, and/or a time lag expected due to physiological and/or environmental parameters monitored by medical system 100, such as heart rate, blood pressure, posture, time of day or night, respiration rate, manual inputs relating to diet, and/or other physiological and/or environmental parameters.

Processing circuitry 106 may be configured to group the given training input vector and the associated training output vector into a data pair. In examples, processing circuitry 106 formulates a plurality of training input vectors indicative of a cardiac signal, a cardiac segment, and/or a cardiac marker received from cardiography system 114 for patient 104 and associates a training output vector indicative of a glucose signal received from glucose sensor 110 for each training input vector. Processing circuitry 106 may group each training input vector and associated training output vector in a data pair, such that processing circuitry 106 formulates a plurality of data pairs. Processing circuitry 106 may define a training data set using the plurality of data pairs. Thus, processing circuitry 106 may be configured to define the training data set using data pairs substantially personalized to the physiology of patient 104.

Processing circuitry 106 uses the training data set formulated to train a machine learning algorithm (162). Processing circuitry 106 may include one or more processing circuits configured to implement the machine learning algorithm, such as a neural network, a deep learning system, or another type of machine learning system. In examples, processing circuitry 106 is configured to implement the machine learning algorithm using one or more neural network systems, deep learning systems, or other types of supervised or unsupervised machine learning systems. For example, the machine learning algorithm may be implemented by a feedforward neural network, such as a convolutional neural network, a radial basis function neural network, a recurrent neural network, a modular or associative neural network. Processing circuitry 106 trains the machine learning algorithm using the training data set personalized to patient 104. In some examples, the machine learning algorithm may be pre-trained to some degree using data indicative of physiological characteristics gathered from a cohort of patients, and processing circuitry 106 may be configured to further train the machine learning algorithm using the training data set personalized to patient 104.

In examples, a neural network utilized by processing circuitry 106 includes a plurality of artificial neurons. The artificial neurons may be present within one or more layers of the neural network. For example, the artificial neurons may present within an input layer of the neural network, an output layer of the neural network, and one or more hidden layers between the input layer and the output layer. The input layer may include one or more input artificial neurons. The output layer may include one or more output artificial neurons. The artificial neurons may be configured to receive a signal at an input of the artificial neuron and process the signal at an output of the artificial neuron (e.g., process the signal using a parameter of the artificial neuron). The artificial neuron may include a plurality of inputs and a plurality of outputs. The artificial neuron may be configured to receive the input from the output of a separate artificial neuron, and may be configured to pass the processed signal from its output to the input of another artificial neuron. The processing of the signal conducted by the artificial neuron may be adjusted by the artificial neuron as training of the machine learning algorithm proceeds.

Processing circuitry 106 is configured to train the machine learning algorithm using the training data set formulated. In examples, processing circuitry 106 is configured to provide one or more elements of a training input vector of the formulated training data set to the inputs of one or more input artificial neurons. The machine learning algorithm may be configured to provide an resulting output vector at the outputs of one or more output artificial neurons subsequent to processing circuitry 106 providing the training input vector to the inputs. The processing circuitry may be configured to provide one or more elements of the training output vector associated with the training input vector as a desired output. In examples, the machine learning algorithm is configured to determine an error between the resulting output vector produced using the training input vector and the desired output of the associated training output vector. The machine learning algorithm may be configured to adjust the processing employed by an artificial neuron (e.g., adjust the parameter) when the artificial neuron processed a signal received at its input to generate a processed signal at its output. In examples, the machine learning algorithm may be configured to adjust the processing employed by a plurality of artificial neurons. In examples, processing circuitry 106 is configured to train the machine learning algorithm such that when processing circuitry 106 provides an input vector indicative of a cardiac signal of patient 104, the trained machine learning algorithm maps the input vector to an output vector indicative of a representative glucose level of patient 104.

Processing circuitry 106 may be configured to train the machine learning algorithm using the training data set in any manner causing the machine learning algorithm to converge as the training proceeds. In examples, processing circuitry 106 is configured to use a first portion of the training data set to cause the machine learning algorithm to converge and a second portion of the training data set to validation test and/or blind test the training conducted with the first portion.

Processing circuitry 106 is configured to utilize the trained machine learning algorithm to provide a representative glucose level of patient 104 based on a current cardiac signal received from cardiography system 114 (164). For examples, using the trained machine learning algorithm, processing circuitry 106 may receive a cardiac signal of patient 104 from cardiography system 114 and formulate an input vector having one or more elements indicative of the cardiac signal. Processing circuitry 106 may be configured to provide the input vector to the trained machine learning algorithm and utilize the trained machine learning algorithm to map the input vector to a representative glucose level. Processing circuitry 106 may be configured to provide the representative glucose level as an output to a user interface. The user interface may be configured to display the representative glucose level in a format viewable by patient 104. In examples, processing circuitry may be configured to store the representative glucose level in a memory included within medical system 100, and/or communicate the representative glucose level to a server and/or one or more other computing devices.

In examples, processing circuitry 106 is configured to periodically perform a calibration check of the trained machine learning algorithm by determining a current glucose level of patient 104 using glucose sensor 110 and comparing the current glucose level to a representative glucose level determined for patient 104 using the trained machine learning algorithm. In examples, processing circuitry 106 receives a current cardiac signal of patient 104 from cardiography system 114 and formulates an input vector having one or more elements indicative of the current cardiac signal. Processing circuitry 106 provide the input vector to the trained machine learning algorithm and utilizes the trained machine learning algorithm to map the input vector to a representative glucose level. Processing circuitry 106 further receives a glucose signal indicative of a current glucose level of patient 104 from glucose sensor 110. Processing circuitry 106 may be configured to compare the current glucose level of patient 104 indicated by glucose sensor 110 with the representative glucose level determined by the trained machine learning algorithm using the current cardiac signal. Based on the comparison, processing circuitry 106 may be configured to formulate additional training data and further train or re-train the machine learning algorithm using the additional training data. For example, processing circuitry 106 may be configured to formulate additional training data by performing one or more of receiving a cardiac signal indicative of a cardiac characteristic of heart 102 from cardiography system 114 (152), activating glucose sensor 110 (154), receiving a glucose signal from glucose sensor 110 (156), deactivating glucose sensor 110 (158), formulating additional training data (160), and re-training and/or further training the machine learning algorithm using the additional training data (162).

Processing circuitry 106 may be prompted to perform a calibration check by any criteria. In examples, processing circuitry is configured to perform a calibration check on a chronological schedule, such as following the elapse of a certain amount of time between calibration checks. In examples, processing circuitry 106 is configured to perform a calibration check based on changes in the cardiac signal, such as unexpected changes between specific cardiac markers. For example, if two or more independent cardiac markers which normally move in concert with a glucose level begin to exhibit movement in opposite and/or unexpected directions relative to each other, processing circuitry 106 may be configured to perform a calibration check. Processing circuitry 106 may be configured to perform a calibration check based on changes in a glucose level sensed by glucose sensor 110 relative to changes in one or more cardiac markers determined from a cardiac signal from cardiaography system 114. Processing circuitry 106 may be configured to perform a calibration check under any criteria which may be defined using the glucose signal from glucose sensor 110, the cardiac signal from cardiography system 114, and/or other physiological parameters of patient 104. Processing circuitry 106 may be configured to activate glucose sensor 110 when a calibration check is required, and/or when the calibration check indicates further training and/or retraining of the machine learning algorithm may be necessary.

Hence, medical system 100 is configured to collect a one or more cardiac signals indicative of cardiac characteristics of patient 104 from cardiography system 114 (e.g., sensing circuitry 116) and one or more glucose signals indicative of glucose levels of patient 104 from glucose sensor 110. Processing circuitry 106 is configured to formulate a training data set using the cardiac signals and the glucose signals produced by patient 104. Processing circuitry 106 is configured to train a machine learning algorithm using the training data set. In examples, the training data set includes a plurality of training input vectors indicative of the cardiac signals and an associated training output vector indicative of the glucose signals. Subsequent to the training, medical system 100 is configured to receive a current cardiac signal from cardiography system 114 and use the trained machine learning algorithm to map the current cardiac signal to a representative glucose level of patient 104. Medical system may cause glucose sensor 110 to deactivate when the glucose signals are no longer actively required (e.g., once the training data set is formulated, and/or once the machine learning algorithm is trained). Thus, medical system 100 may be configured to substantially reduce and/or minimize the activated time of an on-board glucose sensor, potentially extending the life of the glucose sensor and decreasing the need for periodic replacement.

Processing circuitry 106 may be configured to deactivate glucose sensor 110 to prevent and/or minimize the electrical power received by the electrode. Deactivating glucose sensor 110 to reduce and/or substantially prevent the oxidation of glucose may extend the life of the electrode by reducing degradation of the included catalyst, or other portions of glucose sensor 110. For example, processing circuitry 106 may be configured to activate glucose sensor 110 when one or more glucose signals are required to formulate the training data set and/or perform a calibration check of the trained machine learning algorithm, and may be configured to deactivate glucose sensor 110 when processing circuitry 106 utilizes the trained machine learning algorithm and a current cardiac signal from cardiography system 114 (e.g., sensing circuitry 116) to determine a representative glucose level.

Figure 3:
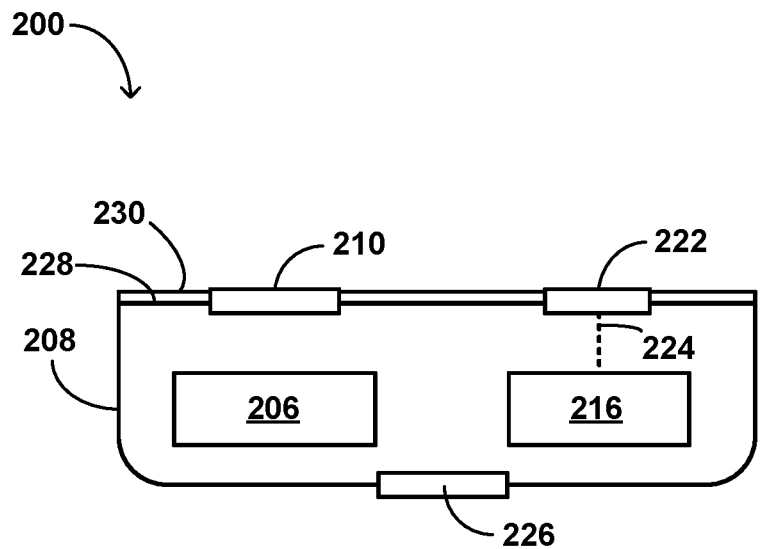
FIG. 3 is a conceptual diagram of a medical system including sensing circuitry.

In examples, housing 108 of medical system 100 mechanically supports one or more of processing circuitry 106, glucose sensor 110, and/or sensing circuitry 116. For example, FIG. 3 illustrates an example medical system 200 including a housing 208. Medical system 200 is an example of medical system 100. Housing 208 mechanically supports processing circuitry 206 and glucose sensor 210. In examples, housing 208 mechanically supports sensing circuitry 216. Housing 208 may be configured as a wearable, implantable, and/or portable device configured to contact a body (e.g., a torso) of patient 104 (FIG. 1). In some examples, the medical system 200 includes one or more electrodes 222 configured to contact patient 104 and sense a cardiac characteristic of heart 102. Electrodes 222 may be configured to communicate the cardiac characteristic to sensing circuitry 216 via, e.g., a communication link 224. Housing 208 may mechanically support electrodes 222. In some examples, housing 208 mechanically supports electrode 222 and/or glucose sensor 210 such that electrode 222 and/or glucose sensor 210 may substantially contact the body of patient 104 when housing 208 contacts the body of patient 104. Housing 208, processing circuitry 206, glucose sensor 210, and sensing circuitry 216 are examples of housing 108, processing circuitry 106, glucose sensor 210, and sensing circuitry 116 respectively.

Housing 208 may mechanically support a user input device 226 configured to be actuated by patient 104 and/or another user as needed. User input device 226 may be, for example, a manually operated button on housing 108, and/or circuitry configured to receive a communication (e.g., a wireless communication) from a smart phone, tablet, another external device, and/or some other device configured for receiving user input. In examples, user input device 226 is a multipurpose user interface configured to initiate multiple operations of medical system 200. For example, user input device 226 may be configured to cause one or more of the following functions, without limitation: waking up processing circuitry 206, sensing circuitry 216, and/or other components of medical system 200; triggering sensing circuitry 216 and/or electrode 222 to provide one or more cardiac signals to processing circuitry 206, activating glucose sensor 210 to cause glucose sensor 210 to provide one or more glucose signals to processing circuitry 206, deactivating glucose sensor 210 to cause glucose sensor 210 to cease providing glucose signals to processing circuitry 206, triggering processing circuitry 206 to formulate a training data set and/or train the machine learning algorithm, triggering processing circuitry to perform a calibration check of the trained machine learning algorithm, and the like.

User input device 226 may employ any device to receive an input from patient 104 and/or another user, including one or more of a button, a slider mechanism, a pin, a lever, a switch, a touch-sensitive element, and the like. User input device 226 may be configured to receive a communication from a device remote from housing 208 (e.g., a wireless communication) to initiate performance of one or more of the above-described functions, or other functions. In some examples, medical system 200 includes more than one user input device 226 to initiate the various functions described above.

In examples, medical system 200 is a portable device. Medical system 200 may be a wearable and/or implantable device configured to be worn by patient 104. Medical system 200 may include a base surface 228 configured to face and/or contact the skin of patient 104 when medical system 200 is worn by patient 104. Housing 208 may be configured to mechanically support glucose sensor 210 and/or electrode 222 such that at least some portion of glucose sensor 210 and/or electrode 222 contacts patient 104 when base surface 228 faces and/or contacts the skin of patient 104. In some examples, medical system 200 includes an adhesive element 230 configured to substantially affix (e.g., temporarily adhere) the housing 208 to the body of patient 104. Adhesive element 230 may be, for example, a piece of double-sided adhesive tape cut into a desired shape and size, and an adhesive liner overlying some portion of base surface 228, or some other type of adhesive element. In some examples, medical system 200 includes one or more straps and/or other mechanical devices to substantially affix the housing 208 to the body of patient 104.

As discussed, processing circuitry 106, 206 may be configured to identify one or more cardiac markers using the cardiac signal received from sensing circuitry 116, 216. Processing circuitry may be configured to identify variabilities in the one or more cardiac markers. In examples, a cardiac marker identified by processing circuitry 106, 206 using the cardiac signal is indicative of changes in autonomic status of heart 102, such as heart rate variability, acceleration and deceleration capacity and/or heart rate turbulence. A cardiac marker may be indicative of an arrhythmia of heart 102. In examples, a cardiac marker may be selected to reflect changes in the sympathetic and/or parasympathetic drive of heart 102, such as an increased sympathetic drive and/or a decreased parasympathetic drive. In some examples, a cardiac marker is indicative of a low frequency band of heart rate variability and/or of an acceleration capacity (e.g., to reflect the sympathetic drive of heart 102). In some examples, a cardiac marker is indicative of a high frequency band of heart rate variability and/or of a deceleration capacity (e.g., to reflect the parasympathetic drive of heart 102). A cardiac marker may be indicative of a heart rate turbulence (HRT) of heart 102 (e.g., a turbulence onset (TO) and/or a turbulence slope (TS)) determined using, for example, the heart rate after premature beats to assess acceleration and deceleration. In examples, a cardiac marker is indicative of a deceleration capacity (DC) and/or a deceleration run (DR).

In examples, a cardiac marker identified by processing circuitry 106 using the cardiac signal is indicative of a cardiomyopathy. The cardiomyopathy may be characterized by, for example, a left ventricular hypertrophy, and/or other physiological characteristics of heart 102. In examples, a cardiac marker is at least one of a heart rate variability (HRV), a QT internal variability (QTV), a corrected QT interval (QTc and/or QTt), an ST interval, an ST elevation, a T wave amplitude, a T-peak to T-end interval, a T slope, a T-wave area, a T-wave asymmetry, an R-wave amplitude, a T-wave amplitude, an R-wave/T-wave amplitude, and/or another identifiable physiological characteristic of the cardiac signal of patient 104. A cardiac marker identified may include a T-wave *alternans* based on two or more T-waves (e.g., by beat-to-beat envelop analyses). In some examples, a cardiac marker identified by processing circuitry 106, 206 using the cardiac signal includes a T-wave area variability including the dimensions of start ending, height slope, and/or symmetry.

A cardiac marker identified by processing circuitry 106, 206 using the cardiac signal may be an HRV time-domain interval measure and/or an HRV frequency domain measure. For example a cardiac marker may be HRV time domain interval measure based on a Normal-to-Normal (NN) interval between R peaks of the cardiac signal, such as an SDNN (e.g., standard deviation of NN intervals), SDANN (e.g., standard deviation of the averages of NN intervals over a time segment (e.g., 5 mins)), an RMSSD (e.g., square root of the mean of a sum of squares of differences between NN intervals), an NN50 (e.g., number of pairs of adjacent NN intervals differing by more than 50 ms), a pNN50 (e.g., NN50 count divided by a number of NN intervals), a mNN (e.g., a means of NN intervals), an SDNNindex (e.g., a mean of the standard deviations of NN intervals over a time segment (e.g., 5 mins)), an SD1 (e.g., a pointcare plot of short term variability), an SD22 (e.g., a pointcare plot of long term variability), and/or other time domain interval measures. A cardiac marker may be HRV frequency time domain measure reflecting a physiological parameter of heart 102 in an LF band of from about 0.15 Hz to about 0.04 Hz, a VLF band from about 0.04 Hz to about 0.003 Hz, a ULF band less than about 0.003 Hz, and/or an HF band of from about 0.4 Hz to about 0.15 Hz.

Processing circuitry 106, 206 may be configured to determine a representative glucose level using, for example, the one or more cardiac markers, and/or variabilities in the one or more cardiac markers. In examples, processing circuitry 106, 206 is configured to identify a plurality of cardiac markers using the cardiac signal and assign a weight to each of the cardiac markers. The machine learning algorithm may be configured to adjust a weight assigned to a cardiac marker when processing circuitry 106, 206 trains the machine learning algorithm. Processing circuitry 106. 206 and/or the machine learning algorithm may be configured to adjust and/or correct the one or more cardiac markers based on characteristics specific to patient 104, such as activity level, medication, respiration level, heart rate, age, gender, weight, ST segment changes, time of day (e.g., nocturnal and/or diurnal), comorbidities and/or disease progression, diabetes 1, diabetes 2, and/or other specific characteristics.

As discussed, medical system 100, 200 includes one or more glucose sensors 110, 210 configured to periodically and/or substantially continuously communicate a glucose signal indicative of the glucose level of patient 104 to processing circuitry 106. Glucose sensors 110, 210 may be configured to generate the glucose signal indicative of the glucose level in any manner, including sensing of electrochemical potentials, near-infra-red spectroscopy, impedance spectroscopy, Raman spectroscopy, tomography, photoacoustics, and other methods.

Processing circuitry 106 may be configured to activate and de-activate glucose sensor 110, 210 in order to, for example, extend an operational life of glucose sensor 110, 210. For example, glucose sensor 110, 210 may be configured to cause an oxidation of glucose using a catalyst such as a glucose oxidase enzyme. Degradation of the catalyst as a result of normal sensing operation of the individual glucose sensor may substantially limit the operational life of the individual glucose sensor available. Deactivating glucose sensor 110, 210 to reduce and/or substantially prevent the oxidation of glucose may extend the life of the electrode by reducing degradation of the included catalyst, or other portions of glucose sensor 110, 210. Such selective activation and deactivation may extend the useful life of glucose sensor 110, 210.

In an example, glucose sensor 110, 210 includes one or more electrodes necessary for the sensing of glucose within the blood and/or interstitial fluid of patient 104. The one or more electrodes may include a working, reference, and/or counter electrode. The working electrode may include an electrochemical sensing stack including an analyte sensing layer, such as an enzyme layer, for example a glucose oxidase layer. For example, the enzyme layer may be deposited on the working electrode. In certain embodiments, the electrochemical sensing stack may include additional layers, such as a protein layer including a protein such as human serum albumin, bovine serum albumin or the like. The electrochemical sensing stack 50 may further includes an analyte modulating layer, such as a glucose limiting membrane (GLM), over the enzyme layer to regulate analyte contact with the analyte sensing layer or enzyme layer. For example, the analyte modulating membrane layer may be configured to substantially regulate the amount of glucose that contacts an enzyme such as glucose oxidase present in the analyte sensing layer.

Figure 4:
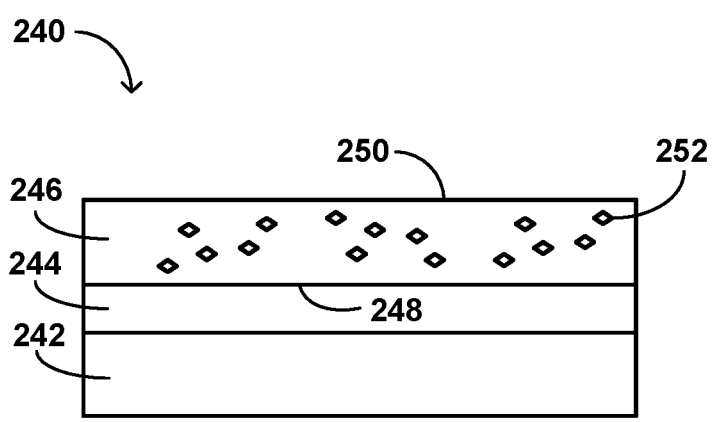
FIG. 4 is a conceptual diagram of an electrode of a glucose sensor.

As an example, FIG. 4 illustrates a cross sectional of an example sensor electrode 240 which may be included in glucose sensor 110, 210 for the detection of glucose in blood and/or interstitial fluid of patient 104. Sensor electrode 240 may be formed from a plurality of components that are typically in the form of layers of various conductive and non-conductive constituents disposed on each other according to accepted methods, although other configurations for sensor electrodes included in glucose sensor 110, 210 may be utilized.

In the example illustrated in FIG. 4, sensor electrode 240 includes a base layer 242 to support one or more portions of sensor electrode 240. Base layer 242 may comprise, for example, a material such as a polymeric substrate, which may be self-supporting or further supported by another material. Base layer 242 may be a non-toxic biocompatible polymer, such as silicone compounds, polyimides, biocompatible solder masks, epoxy acrylate copolymers, or the like. An exemplary base layer 242 is polyethylene terephthalate (PET), polyimide (PI), or a composite thereof. Sensor electrode 240 may include a conductive layer 244 disposed over, and/or directly on and/or combined with, base layer 242. An exemplary conductive layer 244 is platinum. Base layer 242 and/or conductive layers 244 may be generated using many known techniques and materials. In certain embodiments, an electrical circuit of glucose sensor 110, 210 is defined by etching the disposed conductive layer 244 into a desired pattern of conductive paths. An electrically insulating layer may be formed around and/or on some portion of conductive layer 244. For example, the electrically insulating layer may be a polymer coating, such as non-toxic biocompatible polymers such as silicone compounds, polyimides, biocompatible solder masks, epoxy acrylate copolymers, or the like.

Sensor electrode 240 may be configured such that conductive layer 244 is exposed to an external environment. In examples, an analyte sensing layer 246 is formed over and/or is disposed on an exposed electrode surface 248. Sensing layer 246 may be a sensor chemistry layer including materials which undergo a chemical reaction and/or participate in a series of chemical reactions that generate a signal sensed by conductive layer 244. Sensing layer 246 may form a sensor surface 250 where an analyte such as glucose may bind. In some examples, sensing layer 246 includes an enzyme 252 which catalyzes some portion of the chemical reaction and/or the series of chemical reactions. Enzyme 252 may be entrapped within a polymer matrix (e.g., a thermally-cured polymer matrix and/or UV-cured polymer matrix) of sensing layer 246. Enzyme 252 may be an material capable of producing and/or utilizing oxygen and/or hydrogen peroxide, such as the enzyme glucose oxidase. In examples, sensor electrode 240 includes a glucose limiting membrane configured to limit an amount of glucose which reaches sensing layer 246 and/or enzyme 252. The glucose limiting membrane may be configured to limit an amount of glucose which reaches sensor surface 250. In examples, the glucose limiting membrane is configured to limit and/or modulate a glucose signal provided by a glucose sensor such as glucose sensor 110, 210.

In examples, the enzyme 252 such as glucose oxidase in the sensing layer 246 reacts with glucose to produce hydrogen peroxide, a compound which then modulates a current at the electrode surface 248. As this modulation of current depends on the concentration of hydrogen peroxide, and the concentration of hydrogen peroxide correlates to the concentration of glucose, the concentration of glucose can be determined by monitoring this modulation in the current. In a specific embodiment, the hydrogen peroxide is oxidized at an electrode surface 248 that is an anode (also termed herein the anodic electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector.

Glucose sensor 110, 210 may be configured to sense a glucose level in the blood and/or interstitial fluid of patient 104 using electrode 240. Glucose sensor 110, 210 may be configured to sense the glucose level using electrode 240 in conjunction with one or more other electrodes, such as a working electrode and/or reference electrode. Glucose sensor 110, 210 may be configured to bring the blood and/or interstitial fluid of patient 104 into contact with sensing layer 246 to cause the chemical reaction and/or series of chemical reactions generating a signal (e.g., a current at electrode surface 250).

With continued use of glucose sensor 110, 210, the accuracy and/or sensitivity of glucose sensor 110, 210 for the detection of glucose within blood and/or interstitial fluid of patient 104 may drift due to degradation caused by exposure to various electroanalytical species such as oxygen radicals. Further, post-implantation effects such as biofouling and foreign body response may also contribute to passivation of the electro catalytic activity of one or more of the electrodes comprising glucose sensor 110, 210. Thus, the useful life of glucose sensor 110, 210 may act to limit the lifetime over which medical system 100, 200 may be consistently employed. In examples, and as discussed, medical system 100, 200 is configured to extend an operational life of glucose sensor 110, 210 by activating glucose sensor 110, 210 when glucose signals are required (e.g., when formulating a training data set and/or performing a calibration check), and deactivating glucose sensor 110, 210 when the glucose signals are no longer required (e.g., when the trained machine learning algorithm is used to determine representative glucose levels).

In some examples, glucose sensor 110, 210 includes a plurality of individual glucose sensors and processing circuitry 106 is configured to selectively activate a first portion (e.g., a first individual glucose sensor) of the individual glucose sensors to generate the glucose signal. Processing circuitry 106, 206 may be configured to retain a second portion of the plurality individual glucose sensors in a deactivated state as the first portion generates the glucose signal, such that medical system 100, 200 may receive the glucose signal without potentially degrading the second portion of the plurality. For example, processing circuitry 106, 206 may be configured to activate the first individual glucose sensor by exposing the first individual glucose sensor to the interstitial fluid or blood of patient 104 to generate a glucose signal when required (e.g., while formulating training data and/or conducting a calibration check). Processing circuitry 106, 206 may be configured to deactivate the first individual glucose sensor and activate a second individual glucose sensor in the plurality in the plurality when a replacement criteria for the first individual glucose sensor is met (e.g., when processing circuitry 106, 206 detects a degraded signal from the first individual glucose sensor, following the elapse of a chronological period of use of the first individual glucose signal, and/or for another reason). Including a plurality of individual glucose sensors may extend an operational life of medical system 100, 200 allowing, for example, patient 104 to utilize medical system 100, 200 for a longer period of time prior to replacement.

Figure 5:
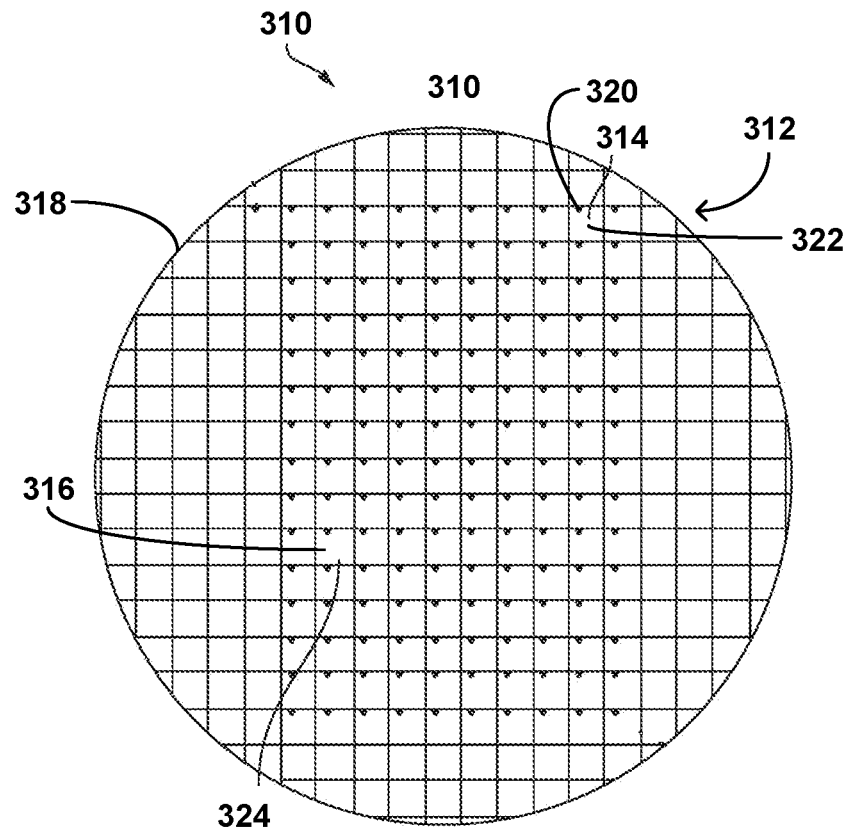
FIG. 5 is a conceptual diagram of a plurality of glucose sensors.

As an example, FIG. 5 is a plan view of a glucose sensor 310 including a plurality of individual glucose sensors 312. Glucose sensor 310 is an example of glucose sensor 110, 210. Glucose sensor 310 may include a base substrate 318 suitable for use in manufacturing a plurality of glucose sensor devices. Each individual glucose sensor may include one or more sensor electrodes such as sensor electrode 240 (FIG. 3). Each individual glucose sensor may include one or more conductive plugs in electrical communication with a conductive layer (e.g., conductive layer 244 (FIG. 3)) of the individual glucose sensor, such as conductive plugs 320 of first individual glucose sensor 314. In some examples, base substrate 318 is a wafer formed from an appropriate material that accommodates waferscale manufacturing, such as a semiconductor material such as silicon, a glass material, a ceramic material, a sapphire material, a polymer material, a plastic material, or a composite material. Base substrate 318 may have any suitable dimensions and/or thickness to accommodate the plurality of individual glucose sensors 312.

In examples, glucose sensor 310 may be configured such that a first individual glucose sensor (e.g., first individual glucose sensor 314) may be exposed to blood and/or interstitial fluid of patient 104 while other individual glucose sensors remain isolated. For example, each individual glucose sensor may be substantially surrounded by a cavity or well, such as cavity 322 substantially surrounding first glucose sensor 310. Cavity 322 may be configured to enclose a volume of fluid (e.g., blood and/or interstitial fluid of patient 104) and establish fluid communication between the volume of fluid and one or more sensor electrodes of first individual glucose sensor 314, such that first individual glucose sensor 314 generates a glucose signal indicative of a glucose level within the volume of fluid. Cavity 322 may be configured to maintain a fluid isolation between the volume of fluid and other individual glucose sensors within the plurality of individual glucose sensors 312, such that the other individual glucose sensors (and any enzymes, e.g., glucose oxidase) are not exposed to the volume of fluid. Processing circuitry 106, 206 may be configured to activate first individual glucose sensor 314 within cavity 322 to generate a glucose signal until a replacement criteria for first individual glucose sensor 314 is met, then activate individual glucose sensor 316 within a cavity 324 to provide the glucose signal. Processing circuitry 106, 206 may be configured to selectively activate individual glucose sensors in this manner for substantially all individual glucose sensors within the plurality of glucose sensors 312 in order to, for example, extend a working life of glucose sensor 110, 210.

Figure 6:
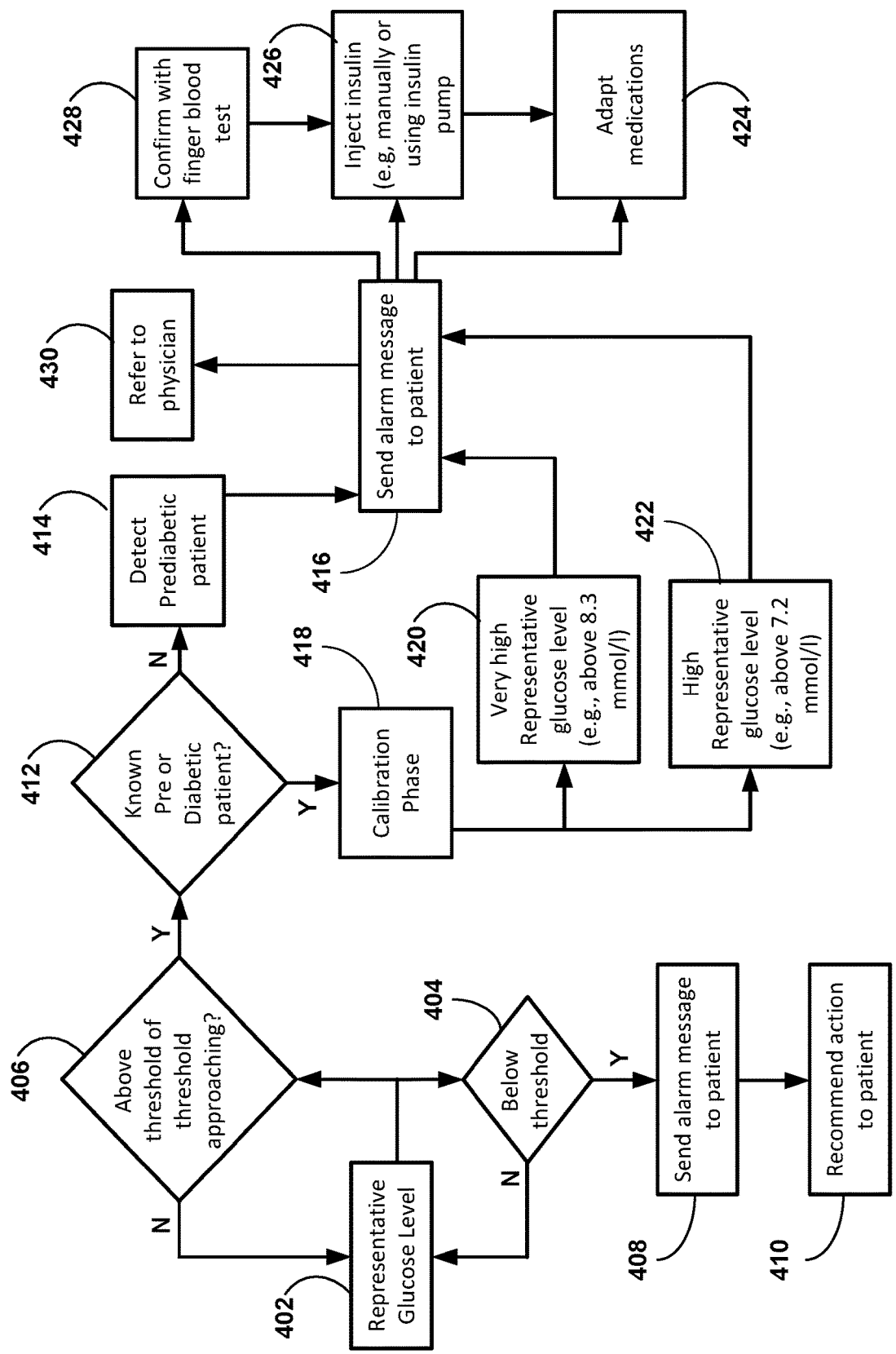
FIG. 6 is a flow diagram for processing circuitry of an example medical system.

FIG. 6 is illustrates a flow diagram of an example technique which may be utilized by processing circuitry 106, 206 based on a representative glucose level of patient 104 determined using a cardiac signal of heart 102. Processing circuitry 106, 206 may be configured to utilize all or any portion of the technique illustrated by FIG. 6.

Processing circuitry 106, 206 may be configured to determine a representative glucose level (402). Processing circuitry 106, 206 may evaluate the representative glucose level to determine if the representative glucose level is below a low threshold (404) and/or to determine if the representative glucose level is above a high threshold and/or trending toward a high threshold (406). The low threshold and/or the high threshold may be generalized levels, or may be specific to patient 104 and/or a subset of patients such as patient 104.

Processing circuitry 106, 206 may be configured to determine another representative glucose level if the representative glucose level is not below the low threshold (N at 404). If the representative glucose level is below the low threshold (Y at 404), processing circuitry 106, 206 may be configured take additional actions. For example, processing circuitry 106, 206 may be configured to send a low threshold alarm to patient 104 (e.g., using a user interface) and/or a clinician (408). Processing circuitry 106, 206 may be configured to send the low threshold alarm via a portable and/or wearable medical device, a smart phone, a tablet, another processor or computing system, or another external device. Processing circuitry 106, 206 may be configured to recommend an action to be taken by patient 104 (410), such as ingesting orange juice or taking some other remedial action.

Processing circuitry 106, 206 may be configured to determine another representative glucose level if the representative glucose level is not above the high threshold (N at 406). If the representative glucose level is above the high threshold (Y at 406), processing circuitry 106, 206 may be configured take additional actions. In examples, processing circuitry 106, 206 is configured to evaluate whether patient 104 is a known diabetic or pre-diabetic patient (412). If patient 104 is not a known diabetic or pre-diabetic patient (N at 412), processing circuitry 106, 206 may be configured to detect and/or identify patient 104 as a diabetic or pre-diabetic patient (414). Processing circuitry 106, 206 may be configured to send an alarm message to patient 104 and/or another user or clinician (416) via, for example, a portable and/or wearable medical device, a smart phone, a tablet, another processor or computing system, or another external device.

If patient 104 is known diabetic or pre-diabetic patient (Y at 412), processing circuitry 106, 206 may be configured to calibrate the machine learning algorithm (418) by, for example, formulating additional training data and further training or re-training the machine learning algorithm using the additional training data. Following calibration, processing circuitry 106, 206 may be configured to determine if the representative glucose level of patient 104 indicates a very high glucose level (e.g., above 8.3 mmol/l) (420) or a high glucose level (e.g., above 7.2 mmol/l) (422). Processing circuitry 106, 206 may be configured to send an alarm message to patient 104 and/or another user or clinician (416) based on determining a very high glucose level (420) or high glucose level (422).

Processing circuitry 106, 206 may be configured suggest one or more treatment routes based on the representative glucose level determined for patient 104. For example, the treatment route suggested may be for patient 104 to adapt and/or adjust medication (424). The treatment route suggested may be a recommendation to inject insulin (e.g., manually or automatically) (426). The treatment route suggested may be to confirm the results of processing circuitry 106, 206 using additional testing, such as a finger blood test. (428). The treatment route suggested may be to consult a physician (430).

In examples, processing circuitry 106, 206 is configured to evaluate and/or analyze high thresholds and low thresholds indicated by the representative glucose level of patient 104. Processing circuitry 106, 206 may be configured to evaluate and/or analyze the high thresholds and low thresholds over a certain time window. The time window may be, for example, a floating time window (e.g, a time window having a start time and/or stop time that adjusts as chronological time progresses). In examples, processing circuitry 106, 206 is configured to store the value of the high thresholds and the value of the low thresholds detected. The value of a high threshold and the value of a low threshold may be determined using the representative glucose level.

Figure 7:
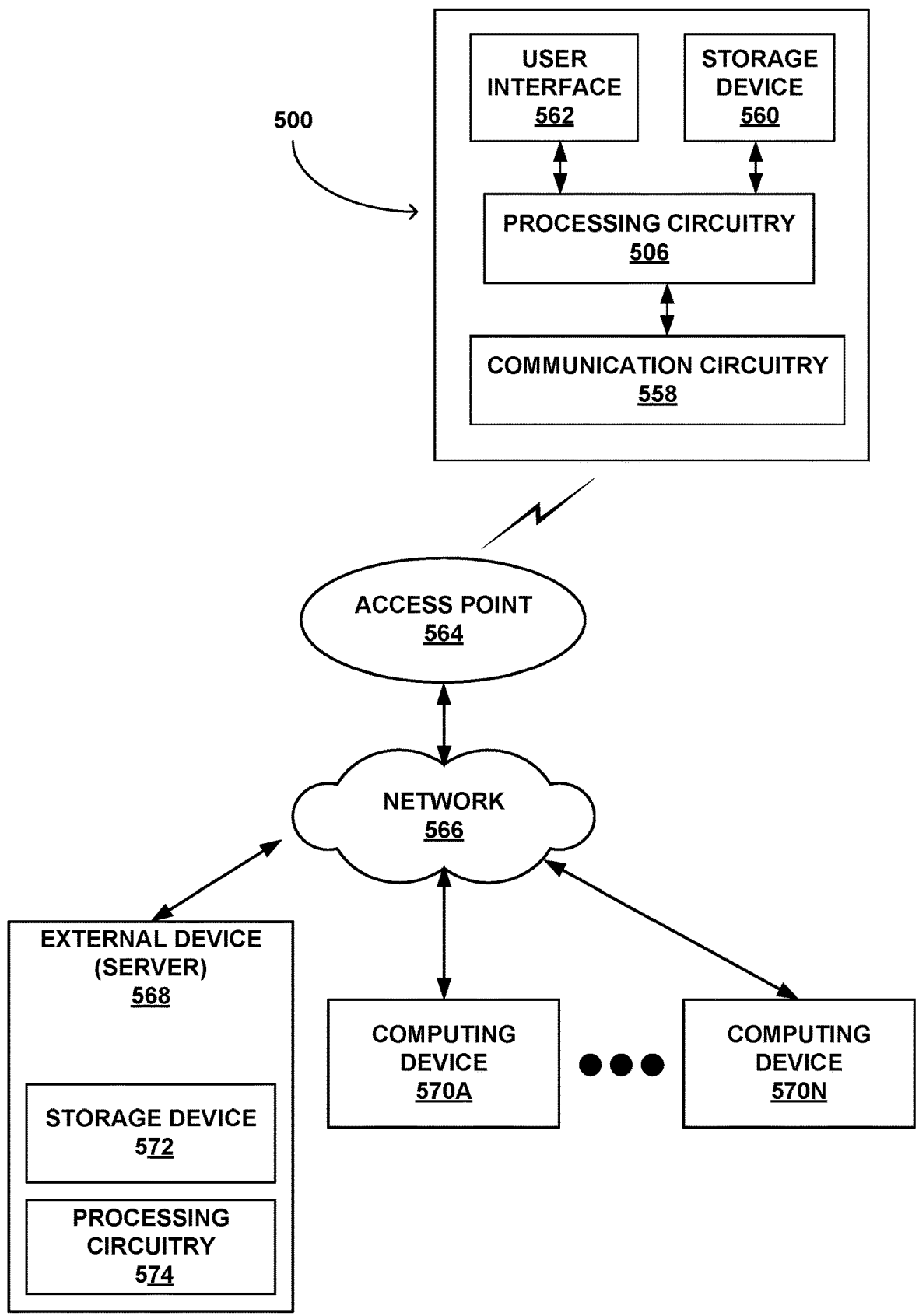
FIG. 7 is a conceptual diagram of a medical system including a network.

FIG. 7 is a block diagram illustrating an example medical system 500 configured to communicate with one or more external systems. Medical system 500 includes processing circuitry 506, communication circuitry 558, storage device 560, and a user interface 562. Medical system 500 is an example of medical system 100, 200 and processing circuitry 506 is an example of processing circuitry 106, 206. Processing circuitry 506 may include one or more processors that are configured to implement functionality and/or process instructions for execution within medical system 500. For example, processing circuitry 506 may be capable of processing instructions stored in storage device 560. Processing circuitry 506 may include, for example, microprocessors, DSPs, ASICs, FPGAs, or equivalent discrete or integrated logic circuitry, or a combination of any of the foregoing devices or circuitry. Accordingly, processing circuitry 506 may include any suitable structure, whether in hardware, software, firmware, or any combination thereof, to perform the functions ascribed herein to processing circuitry 506.

Communication circuitry 558 may include any suitable hardware, firmware, software or any combination thereof for communicating within medical system 500 or with another device and/or system external to medical system 500. Communication circuitry 558 may be configured to receive and/or send communications under the control of processing circuitry 506. In examples, communication circuitry 558 is configured to send and receive communications via communication links 115, 120, 224, and other communication links within medical system 500. In examples, communication circuitry 558 is configured to send communications to and/or receive communications, including downlink and uplink telemetry, from devices and/or system external to medical system 500. Communication circuitry 558 may be configured to transmit or receive signals via inductive coupling, electromagnetic coupling, Near Field Communication (NFC), Radio Frequency (RF) communication, Bluetooth, Wi-Fi, or other proprietary or non-proprietary wireless communication schemes. Communication circuitry 558 may be configured to communicate via any of a variety of forms of wired and/or wireless communication and/or network protocols.

Storage device 560 may be configured to store information within medical system 500 during operation. Storage device 560 may include a computer-readable storage medium or computer-readable storage device. In some examples, storage device 560 includes one or more of a short-term memory or a long-term memory. Storage device 560 may include, for example, RAM, DRAM, SRAM, magnetic discs, optical discs, flash memories, or forms of EPROM or EEPROM. Storage device 560 may be used to store at least a portion of the cardiac signal generated by sensing circuitry 116, 216 and/or the glucose signal generated by glucose sensor 110, 210. In examples, storage device 560 is used to store data indicative of instructions for execution by processing circuitry 506. Storage device 560 may be used by software or applications running within medical system 500 to temporarily store information during program execution.

A user, such as patient 104 or a clinician, may interact with medical system 500 through user interface 562. User interface 562 may include a visual display with which processing circuitry 506 may present information related a representative glucose level determined for patient 104, cardiac signals received from sensing circuitry 116, 216, glucose signals received from glucose sensor 110, 210, other physiological characteristics related to patient 104 such as heart rate, blood pressure, current glucose level (e.g., using glucose sensor 110, 210), and others. In addition, user interface 562 may include an input mechanism configured to receive input from patient 104 and/or a clinician. The input mechanism may include, for example, any one or more of buttons, a keypad (e.g., an alphanumeric keypad), a peripheral pointing device, a touch screen, or another input mechanism that allows the user to navigate through user interfaces presented by processing circuitry 506 and provide input. In other examples, user interface 562 also includes audio circuitry for providing audible notifications, instructions or other sounds to the user, receiving voice commands from the user, or both.

Medical system 500 may be configured to configured to couple to a network 566 (e.g., via an access point 564) in accordance with one or more techniques described herein. For example, medical system 500 may use communication circuitry 558 to communicate with access point 564 via a hard-line or wireless connection. In the example of FIG. 7, medical system 500, access point 564, server 568, and/or computing devices 570A-570N may be interconnected and may communicate with each other through network 566. Access point 564 may include a device that connects to network 566 via any of a variety of connections, such as telephone dial-up, digital subscriber line (DSL), or cable modem connections. In other examples, access point 564 may be coupled to network 566 through different forms of connections, including wired or wireless connections.

Server 568 may be configured to provide a secure storage site for data that has been collected by medical system 500. In some cases, server 568 may assemble data in web pages or other documents for viewing by trained professionals, such as clinicians, via computing devices 570A-570N. In examples, server 568 may comprise one or more servers, a cloud, one or more databases, and/or a data center. Server 568 may include a storage device 572 (e.g., a memory device) to, for example, store data retrieved from medical system 500. Server 568 may include processing circuitry 574 including one or more processors that are configured to implement functionality and/or process instructions for execution within server 568. For example, processing circuitry 574 may be capable of processing instructions stored in storage device 572. Processing circuitry 574 may include, for example, microprocessors, DSPs, ASICs, FPGAs, or equivalent discrete or integrated logic circuitry, or a combination of any of the foregoing devices or circuitry. Storage device 572 may include a computer-readable storage medium or computer-readable storage device. In some examples, storage device 572 includes one or more of a short-term memory or a long-term memory, such as RAM, DRAM, SRAM, magnetic discs, optical discs, flash memories, or forms of EPROM or EEPROM.

In examples, processing circuitry 574 includes or is a portion of processing circuitry 506. Processing circuitry 574 may be configured to perform all of some portion of the functionality described with respect to processing circuitry 506. Medical system 500 may be configured to provide data to server 568 to enable processing circuitry 574 to perform any portion of the functionality described with respect to processing circuitry 506.

Figure 8:
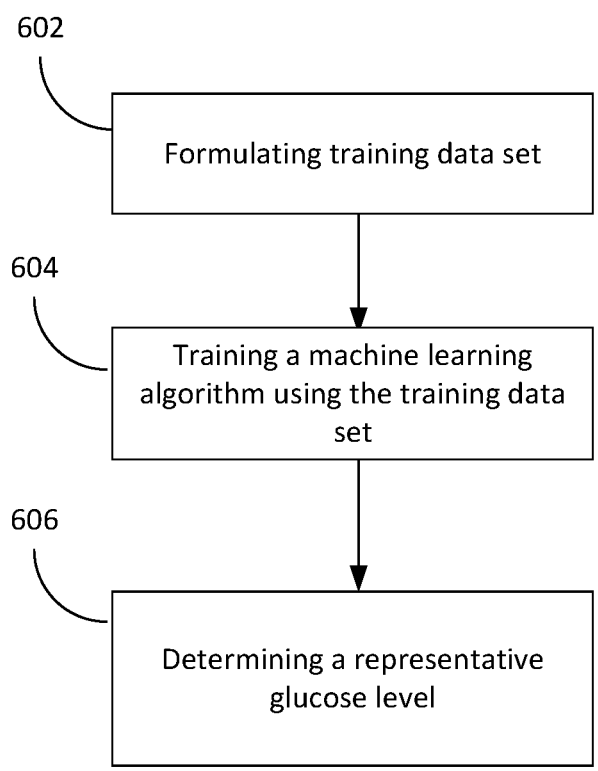
FIG. 8 illustrates an example technique for using a medical system to determine a representative glucose level.

A technique for determining a representative glucose level of a patient is illustrated in FIG. 8. Although the technique is described mainly with reference to medical system 100, 200, 500 of FIGS. 1-7, the technique may be applied to other medical systems in other examples.

The technique includes formulating, using processing circuitry 106, 206, 506, a training data set including one or more training input vectors and one or more training output vectors (602). The technique may include receiving, using processing circuitry 106, 206, 506, a cardiac signal indicative of an cardiac characteristic of a heart 102 of a patient 104 from sensing circuitry 116, 216. The technique may include receiving, using processing circuitry 106, 206, 506, a glucose signal indicate of a glucose level of patient 104 using glucose sensor 110, 210 310. Processing circuitry 106, 206, 506 may be configured to formulate a training input vector including one or more elements representative of the received cardiac signal and a corresponding training output vector including one or more elements of the representative of the received glucose signal.

The technique may include grouping, using processing circuitry 106, 206, 506, a given training input vector and the associated training output vector into a data pair. In examples, processing circuitry 106, 206, 506 is configured to formulate a plurality of training input vectors indicative of a cardiac signal, a cardiac segment, and/or a cardiac marker received from sensing circuitry 116, 216 and associate a training output vector indicative of a glucose signal received from glucose sensor 110, 210, 310 for each training input vector. Processing circuitry 106, 206, 506 may group each training input vector and associated training output vector in a data pair, such that processing circuitry 106, 206, 506 formulates a plurality of data pairs.

The technique includes training, using processing circuitry 106, 206, 506, a machine learning algorithm using the one or more training data sets (604). Processing circuitry 106, 206, 506 may train the machine learning algorithm using one or more neural network systems, deep learning systems, or other types of supervised or unsupervised machine learning systems. The technique may include processing circuitry 106, 206, 506 training the machine learning algorithm using the training data set formulated. In examples, processing circuitry 106, 206, 506 provides one or more elements of a training input vector of the formulated training data set to the inputs of the machine learning algorithm (e.g., to one or more inputs of one or more input artificial neurons in an artificial neural network). The technique may include using the machine learning algorithm to provide an resulting output vector (e.g., an output vector at the outputs of one or more output artificial neurons in the artificial neural network) subsequent to processing circuitry 106, 206, 506 providing the training input vector.

The technique may include comparing, using processing circuitry 106, 206, 506, the training output vector associated with the training input vector with the resulting output vector to determine an error, and adjust the processing employed by the machine learning algorithm based on the error. The technique may include training, using processing circuitry 106, 206, 506, the machine learning algorithm such that when processing circuitry 106, 206, 506 provides an input vector indicative of a cardiac signal of patient 104, the trained machine learning algorithm maps the input vector to an output vector indicative of a representative glucose level of patient 104. In examples, processing circuitry 106, 206, 506 is configured to use a first portion of the training data set to cause the machine learning algorithm to converge and a second portion of the training data set to validation test and/or blind test the training conducted with the first portion.

The technique includes determining, using processing circuitry 106, 206, 506, a representative glucose level of patient 104 using the trained machine learning algorithm (606). The technique may include determining the representative glucose level of patient 104 based on a current cardiac signal received from sensing circuitry 116, 216. In examples, the technique includes receiving a current cardiac signal of patient 104 from sensing circuitry 116, 216 using processing circuitry 106, 206, 506 and formulating, using processing circuitry 106, 206, 506, an input vector having one or more elements indicative of the current cardiac signal. Processing circuitry 106, 206, 506 may provide the input vector to the trained machine learning algorithm and utilize the trained machine learning algorithm to map the input vector to a representative glucose level. In examples, processing circuitry 106, 206, 506 provides the representative glucose level as an output to user interface 562. In examples, processing circuitry 106, 206, 506 stores the representative glucose level in storage device 560 and/or communicates the representative glucose level to a device and/or system external to medical system 100, 200, such as server 568.

The technique may include performing, using processing circuitry 106, 206, 506, a calibration check of the trained machine learning algorithm. Processing circuitry 106, 206, 506 may determine a current glucose level of patient 104 using glucose sensor 110, 210, 310 and compare the current glucose level to a representative glucose level determined for patient 104 using the trained machine learning algorithm. Processing circuitry 106 may receive a current cardiac signal of patient 104 from sensing circuitry 116, 216 and generate a representative glucose level using the current cardiac signal and the trained machine learning algorithm. Processing circuitry 106, 206, 506 may compare the current glucose level of patient 104 indicated by glucose sensor 110, 210, 310 with the representative glucose level determined by the trained machine learning algorithm. Based on the comparison, processing circuitry 106 may formulate additional training data and further train or re-train the machine learning algorithm using the additional training data. For example, processing circuitry 106, 206, 506 may be configured to formulate additional training data by performing one or more of formulating the training data set (602) and training the machine learning algorithm using the training data set (604).

The present disclosure includes the following examples.

Example 1: A medical system comprising: a glucose sensor configured to determine a glucose level in a patient; and processing circuitry operably coupled to the glucose sensor, the processing circuitry configured to: receive a glucose signal indicative of the glucose level from the glucose sensor, receive a cardiac signal indicative of a cardiac characteristic of the patient, associate the glucose signal with the cardiac signal, formulate one or more training data sets including a training input vector and a training output vector, wherein the training input vector is representative of the cardiac signal and the training output vector is representative of the glucose signal associated with the cardiac signal, train a machine learning algorithm using the one or more training data sets, and determine a representative glucose level using the trained machine learning algorithm and a current cardiac signal, wherein the current cardiac signal is indicative of a current cardiac characteristic of the heart of the patient.

Example 2: The medical system of example 1, further comprising sensing circuitry operably connected to the processing circuitry, wherein the sensing circuitry is configured to sense the cardiac characteristic and generate the cardiac signal based on the sensed cardiac characteristic, and wherein the processing circuitry is configured to receive the cardiac signal from the sensing circuitry.

Example 3: The medical system of example 1 or 2, further comprising a portable device configured to be worn by the patient, wherein portable device includes a housing configured to support at least the glucose sensor and the processing circuitry.

Example 4: The medical system of any of examples 1-3, further comprising a plurality of individual glucose sensors, wherein the glucose sensor is one of the individual glucose sensors in the plurality, and wherein the processing circuitry is configured to select the one of the individual glucose sensors.

Example 5: The medical system of any of examples 1-4, the glucose sensor is configured to provide the glucose signal to the processing circuitry in an activated configuration and not provide the glucose signal to the processing circuitry in a deactivated configuration, the glucose sensor is configured to generate the glucose signal using an enzyme, and the processing circuitry is configured to cause the glucose sensor to establish the activated configuration or the deactivated configuration.

Example 6: The medical system of example 5, wherein the glucose sensor includes one or more electrodes configured to detect a reaction product generated from a catalysis of glucose using the enzyme.

Example 7: The medical system of example 5 or 6, wherein the processing circuitry is configured to cause the glucose sensor to establish the deactivated configuration when the processing circuitry determines the representative glucose level using the trained machine learning algorithm and the current cardiac signal.

Example 8: The medical system of any of examples 1-7, wherein the glucose sensor is configured to determine the glucose level in the patient using at least one of near-infrared spectroscopy, impedance spectroscopy, Raman spectroscopy, tomography, or photoacoustics.

Example 9: The medical system of any of examples 1-8, wherein the glucose sensor is configured to determine the glucose level in the patient using at least one of monitoring an optical property of a fluorescent enzyme, monitoring an optical property of a labeled enzymes, monitoring an optical property of a co-enzyme, monitoring an optical property of a co-substrate, measuring a product of enzymatic oxidation of glucose by glucose oxidase, using synthetic boronic acids, using Concanavalin A, or applying glucose-binding proteins.

Example 10: The medical system of any of examples 1-9, wherein the processing circuitry is configured to perform a calibration check by: receiving a current glucose signal from the glucose sensor, wherein the current glucose signal is indicative of a current glucose level in the patient, receiving the current cardiac signal, and comparing the representative glucose level and the current glucose level indicated by the current glucose signal.

Example 11: The medical system of any of examples 1-10, wherein the processing circuitry is configured to perform a calibration check based on one or more of an elapse of a chronological time period, a comparison of a representative glucose level and a current glucose level of the patient, an evaluation of changes in a cardiac marker determined using the cardiac signal, an evaluation of relative changes in two or more cardiac markers determined using the cardiac marker, an evaluation of changes in a glucose signal relative to the cardiac marker determined using the cardiac signal, or an evaluation of a physiological parameter of the patient.

Example 12: The medical system of any of examples 1-11, wherein the processing circuitry is configured to: perform a calibration check of the medical system, formulate one or more additional training data sets based on an evaluation of the calibration check, and conduct additional training of the trained machine learning algorithm using the one or more additional training data sets.

Example 13: The medical system of any of examples 1-12, further comprising a user input device operably coupled to the processing circuitry and configured to cause the processing circuitry to receive the cardiac signal, receive the glucose signal, associate the cardiac signal with the glucose level, formulate the one or more training data sets, train the machine learning algorithm, and determine the representative glucose level.

Example 14: The medical system of any of examples 1-13, wherein the processing circuitry is configured to divide the cardiac signal into a segment, wherein the segment is a portion of the cardiac signal received over a time interval, and wherein the glucose signal associated with the cardiac signal is portion of the glucose signal associated with the time interval.

Example 15: The medical system of any of examples 1-14, wherein the machine learning algorithm is an artificial neural network including one or more input artificial neurons, and wherein the processing circuitry is configured to train the machine learning algorithm by providing the training input vector to the one or more input artificial neurons.

Example 16: The medical system of example 15, wherein: the processing circuitry is configured to provide the training input vector to the machine learning algorithm, the machine learning algorithm is configured to generate a resulting output vector when the processing circuitry provides the training input vector, and the machine learning algorithm is configured to adjust a parameter of one or more artificial neurons within the machine learning algorithm based on a comparison of the resulting output vector and the training output vector.

Example 17: The medical system of any of examples 1-16, wherein: the processing circuitry is configured to identify a cardiac marker using the cardiac signal and associate the cardiac marker with the glucose level, the training input vector is representative of the cardiac marker, and the processing circuitry is configured to determine the representative glucose level using the trained machine learning algorithm and the cardiac marker.

Example 18: The medical system of any of examples 1-17, wherein: the processing circuitry is configured to identify a cardiac marker using the cardiac signal and associate the cardiac marker with the glucose level, and the cardiac marker is at least one of a heart rate variability (HRV), a QT internal variability (QTV), a corrected QT interval (QTc and/or QTt), an ST interval, an ST elevation, a T wave amplitude, a T-peak to T-end interval, a T slope, a T-wave area, a T-wave asymmetry, an R-wave amplitude, a T-wave amplitude, an R-wave/T-wave amplitude, a T-wave *alternans*, a T-wave area variability, a heart rate variability in the time and frequency domain, a heart rate turbulence onset (TO), a turbulence slope (TS), a deceleration capacity (DC), or a deceleration run (DR).

Example 19: The medical system of any of examples 1-18, wherein: the processing circuitry is configured to identify a plurality of cardiac markers using the cardiac signal and assign a weight to each of the cardiac markers, and the processing circuitry is configured to adjust the assigned weights when the processing circuitry trains the machine learning algorithm.

Example 20: The medical system of any of examples 1-19, wherein: the processing circuitry is configured to identify a cardiac marker using the cardiac signal and associate the cardiac marker with the glucose level, and the processing circuitry is configured to correct the cardiac marker based on an activity level of the patient, a medication taken by the patient, a respiration level of the patient, a heart rate of the patient, an age of the patient, a gender of the patient, a weight of the patient, a change in an ST segment of the patient, a time of day, a comorbidity of the patient, a disease of the patient, diabetes 1 of the patient, or diabetes 2 of the patient Example 21: A medical system comprising: a glucose sensor configured to determine a glucose level in a patient; sensing circuitry configured to sense a cardiac characteristic of a heart of the patient; processing circuitry operably coupled to the glucose sensor and the sensing circuitry, the processing circuitry configured to: receive an cardiac signal indicative of the cardiac characteristic from the sensing circuitry, identify a cardiac marker using the cardiac signal, receive a glucose signal indicative of the glucose level from the glucose sensor, associate the cardiac marker with the glucose signal, formulate one or more training data sets including a training input vector and a training output vector, wherein the training input vector is representative of the cardiac signal and the training output vector is representative of the glucose signal associated with the glucose signal, train a machine learning algorithm using the one or more training data sets, and determine a representative glucose level using the trained machine learning algorithm and a current cardiac signal received from the sensing circuitry, wherein the current cardiac signal is indicative of a current cardiac characteristic of the heart of the patient; and a housing mechanically supporting the glucose sensor and the processing circuitry.

Example 22: The medical system of example 21, wherein: the glucose sensor is configured to provide the glucose signal to the processing circuitry in an activated configuration and not provide the glucose signal to the processing circuitry in a deactivated configuration, the glucose sensor is configured to generate the glucose signal using an enzyme, and the processing circuitry is configured to cause the glucose sensor to establish the activated configuration or the deactivated configuration.

Example 23: The medical system of example 21 or 22, wherein the processing circuitry is configured to perform a calibration check by: receiving a current glucose signal from the glucose sensor, wherein the current glucose signal is indicative of a current glucose level in the patient, receiving the current cardiac signal, comparing the representative glucose level and the current glucose level indicated by the current glucose signal, formulating one or more additional training data sets based on the comparison of the representative glucose level and the current glucose level indicated by the current glucose signal, and conducting additional training of the trained machine learning algorithm using the one or more additional training data sets.

Example 24: A method comprising: receiving, using processing circuitry, an ECG signal indicative of an electrocardiogram of a heart of a patient from sensing circuitry configured to sense the electrocardiogram, receiving, using the processing circuitry, a glucose signal indicative of a glucose level of the patient from a glucose sensor configured to determine the glucose level in the patient, associating, using the processing circuitry, the ECG signal with the glucose level, formulating, using the processing circuitry, one or more training data sets including a training input vector and a training output vector, wherein the training input vector is representative of the ECG signal and the training output vector is representative of the glucose signal associated with the ECG signal, training, using the processing circuitry, a machine learning algorithm using the one or more training data sets, and determining, using the processing circuitry, a representative glucose level using the trained machine learning algorithm and a current cardiac signal, wherein the current cardiac signal is indicative of a current cardiac characteristic of the heart of the patient.

Example 25: The method of example 24, further comprising: establishing, using the processing circuitry, the glucose sensor in an activated configuration, wherein the glucose sensor is configured to generate the glucose signal in the activated configuration, receiving the glucose signal with the glucose sensor in the activated configuration, establishing, using the processing circuitry, the glucose sensor in a deactivated configuration, wherein the glucose sensor is configured to not generate the glucose signal in the deactivated configuration, and determining the representative glucose level with the glucose sensor in the deactivated configuration.

Various examples of the disclosure have been described. Any combination of the described systems, operations, or functions is contemplated. These and other examples are within the scope of the following claims.

What is claimed is:

1. A medical system comprising:
   sensing circuitry configured to sense a cardiac characteristic of a patient; and
   processing circuitry configured to:
     receive a current cardiac signal indicative of the cardiac characteristic from the sensing circuitry, wherein the current cardiac signal is indicative of a current cardiac characteristic of the patient, and
     determine a representative glucose level using a machine learning algorithm and the current cardiac signal,
     wherein, previous to determining the representative glucose level, the machine learning algorithm was trained using one or more training data sets including a training input vector and a training output vector, wherein the training input vector is representative of a cardiac signal and the training output vector is representative of a glucose level associated with the cardiac signal.

2. The medical system of claim 1, wherein the training output vector is representative of a glucose signal of a glucose sensor, wherein the glucose signal is representative of the glucose level associated with the cardiac signal.

3. The medical system of claim 1, further comprising a glucose sensor configured to determine a glucose level of the patient.

4. The medical system of claim 3, wherein the processing circuitry is configured to:
   receive a glucose signal indicative of the glucose level of the patient from the glucose sensor;
   receive the cardiac signal from the sensing circuitry, wherein the cardiac signal is indicative of the cardiac characteristic of the patient; and
   formulate at least one of the one or more training data sets by:
     associating the glucose signal with the cardiac signal, and
     formulating the training input vector and the training output vector, wherein the training input vector is representative of the cardiac signal and the training output vector is representative of the glucose signal associated with the cardiac signal.

5. The medical system of claim 3, further comprising a plurality of individual glucose sensors, wherein the glucose sensor is one of the individual glucose sensors in the plurality, and wherein the processing circuitry is configured to select the one of the individual glucose sensors.

6. The medical system of claim 3, wherein:
   the glucose sensor is configured to provide a glucose signal indicative of the glucose level of the patient to the processing circuitry in an activated configuration and not provide the glucose signal to the processing circuitry in a deactivated configuration, and
   the processing circuitry is configured to cause the glucose sensor to establish the activated configuration or the deactivated configuration.

7. The medical system of claim 3, further comprising a portable device configured to be worn by the patient, wherein the portable device includes a housing configured to support at least one of the glucose sensor, the sensing circuitry, or the processing circuitry.

8. The medical system of claim 1, wherein the processing circuitry is configured to train the machine learning algorithm using the one or more training data sets.

9. The medical system of claim 1, wherein at least one of the one or more training data sets is indicative of the physiological characteristics of a cohort of patients.

10. The medical system of claim 1, wherein the processing circuitry is configured to perform a calibration check by:
    receiving a current glucose signal from a glucose sensor, wherein the current glucose signal is indicative of a current glucose level in the patient,
    receiving the current cardiac signal, and
    comparing the representative glucose level and the current glucose level indicated by the current glucose signal.

11. The medical system of claim 1, wherein the processing circuitry is configured to perform a calibration check based on one or more of an elapse of a chronological time period, a comparison of a representative glucose level and a current glucose level of the patient, an evaluation of changes in a cardiac marker determined using the cardiac signal, an evaluation of relative changes in two or more cardiac markers determined using the cardiac marker, an evaluation of changes in a glucose signal relative to the cardiac marker determined using the cardiac signal, or an evaluation of a physiological parameter of the patient.

12. The medical system of claim 1, wherein the processing circuitry is configured to:
    perform a calibration check of the medical system,
    formulate one or more additional training data sets based on an evaluation of the calibration check, and
    conduct additional training of the trained machine learning algorithm using the one or more additional training data sets.

13. The medical system of claim 1, further comprising a user input device operably coupled to the processing circuitry and configured to cause the processing circuitry to at least one of receive the current cardiac signal, receive a glucose signal from a glucose sensor, associate the current cardiac signal with the glucose signal, formulate at least one training data set using the current cardiac signal and the glucose signal, train the machine learning algorithm, or determine the representative glucose level.

14. The medical system of claim 1, wherein the processing circuitry is configured to divide the cardiac signal into a segment, wherein the segment is a portion of the cardiac signal received over a time interval, and wherein the glucose signal associated with the cardiac signal is portion of the glucose signal associated with the time interval.

15. The medical system of claim 1, wherein:
    the processing circuitry is configured to provide the training input vector to the machine learning algorithm,
    the machine learning algorithm is configured to generate a resulting output vector when the processing circuitry provides the training input vector, and
    the machine learning algorithm is configured to adjust a parameter of one or more artificial neurons within the machine learning algorithm based on a comparison of the resulting output vector and the training output vector.

16. The medical system of claim 1, wherein:
    the processing circuitry is configured to identify one or more cardiac markers using the current cardiac signal, and the processing circuitry is configured to determine the representative glucose level using the machine learning algorithm and the one or more cardiac markers.

17. The medical system of claim 16, wherein the processing circuitry is configured to correct at least one of the cardiac markers based on an activity level of the patient, a medication taken by the patient, a respiration level of the patient, a heart rate of the patient, an age of the patient, a gender of the patient, a weight of the patient, a change in an ST segment of the patient, a time of day, a comorbidity of the patient, a disease of the patient, diabetes 1 of the patient, or diabetes 2 of the patient.

18. A medical system comprising:
a plurality of individual glucose sensors, wherein each glucose sensor is configured to determine a glucose level in a patient;
sensing circuitry configured to sense a cardiac characteristic of a heart of the patient;
processing circuitry operably coupled to one or more of the glucose sensors and the sensing circuitry, the processing circuitry configured to:
receive a current cardiac signal indicative of the cardiac characteristic from the sensing circuitry, wherein the current cardiac signal is indicative of a current cardiac characteristic of the patient, and
determine a representative glucose level using a machine learning algorithm and the current cardiac signal,
wherein, previous to determining the representative glucose level, the machine learning algorithm was trained using one or more training data sets including a training input vector and a training output vector, wherein the training input vector is representative of a cardiac signal and the training output vector is representative of a glucose level associated with the cardiac signal; and
a portable device configured to be worn by the patient, wherein the portable device includes a housing configured to support at least one of the plurality of glucose sensors, the sensing circuitry, or the processing circuitry.

19. A method for controlling processing circuitry of a medical system, the method comprising:
receiving, using the processing circuitry, a current cardiac signal indicative of a cardiac characteristic of a heart of a patient from sensing circuitry of the medical system, the sensing circuitry configured to sense the cardiac characteristic; and
determining, using the processing circuitry, a representative glucose level using a machine learning algorithm and the current cardiac signal,
wherein, previous to determining the representative glucose level, the machine learning algorithm was trained using one or more training data sets including a training input vector and a training output vector, wherein the training input vector is representative of a cardiac signal and the training output vector is representative of a glucose level associated with the cardiac signal.

20. The method of claim 19, further comprising:
receiving, by the processing circuitry, a glucose signal indicative of the glucose level of the patient from a glucose sensor of the medical system;
receiving, by the processing circuitry, the cardiac signal from the sensing circuitry, wherein the cardiac signal is indicative of the cardiac characteristic of the patient;
associating, using the processing circuitry, the glucose signal with the cardiac signal; and
formulating the training input vector and the training output vector, wherein the training input vector is representative of the cardiac signal and the training output vector is representative of the glucose signal associated with the cardiac signal.

* * * * *